US00RE42192E

(19) United States
(12) Reissued Patent
Schabron et al.

(10) Patent Number: US RE42,192 E
(45) Date of Reissued Patent: Mar. 1, 2011

(54) VOLATILE ORGANIC COMPOUND SENSOR SYSTEM

(75) Inventors: John F. Schabron, Laramie, WY (US); Joseph F. Rovani, Jr., Laramie, WY (US); Theresa M. Bomstad, Waxahachie, TX (US); Susan S. Sorini-Wong, Laramie, WY (US); Gregory K. Wong, Laramie, WY (US)

(73) Assignee: The University of Wyoming Research Corporation, Laramie, WY (US)

(21) Appl. No.: 12/488,302

(22) Filed: Jun. 19, 2009

Related U.S. Patent Documents

Reissue of:
(64) Patent No.: 7,487,662
Issued: Feb. 10, 2009
Appl. No.: 10/319,090
Filed: Dec. 13, 2002

U.S. Applications:
(60) Provisional application No. 60/405,638, filed on Aug. 23, 2002, and provisional application No. 60/340,561, filed on Dec. 13, 2001.

(51) Int. Cl.

| | |
|---|---|
| ***G01N 27/04*** | (2006.01) |
| ***G01N 27/70*** | (2006.01) |
| ***G01N 27/68*** | (2006.01) |
| ***G01N 1/22*** | (2006.01) |
| ***G01N 33/00*** | (2006.01) |

(52) U.S. Cl. ..... 436/124; 73/1.02; 73/23.2; 422/83; 422/98; 436/3; 436/43; 436/125; 436/126; 436/151; 436/153; 436/181

(58) Field of Classification Search ..... None
See application file for complete search history.

(56) References Cited

U.S. PATENT DOCUMENTS 2,373,111 A * 4/1945 Francis ..... 436/104
2,550,498 A * 4/1951 Rice ..... 324/468
2,652,532 A * 9/1953 Zemany ..... 324/468

(Continued)

FOREIGN PATENT DOCUMENTS

WO 200167086 A 9/2001
WO 200195281 A 12/2001

OTHER PUBLICATIONS

Wander, J., Air Conditioning, Heating & Refrigeration News 1998, 204, 12 and 14.*
Kim, J. B. et al, Journal of Physical Chemistry A 1999, 103, 10833–10841.*
Kram, M. L. et al, Ground Water Monitoring & Remediation 2001, 21, 67–76.*
Kram, M. L. et al, Ground Water Monitoring & Remediation 2001, 21, 109–123.*
Ryan, D. A. et al, Analytical Chemistry 1990, 62, 853–857.*
Potter, D. W. et al, Environmental Science & Technology 1994, 28, 298–305.*

(Continued)

*Primary Examiner*—Arlen Soderquist
(74) *Attorney, Agent, or Firm*—Santangelo Law Offices P.C.

(57) ABSTRACT

Generally, this invention relates to the development of field monitoring methodology for new substances and sensing chemical warfare agents (CWAs) and terrorist substances. It also relates to a portable test kit which may be utilized to measure concentrations of halogenated volatile organic compounds (VOCs) in the field. Specifically it relates to systems for reliably field sensing the potential presence of such items while also distinguishing them from other elements potentially present. It also relates to overall systems and processes for sensing, reacting, and responding to an indicated presence of such substance, including modifications of existing halogenated sensors and arrayed sensing systems and methods.

28 Claims, 18 Drawing Sheets

U.S. PATENT DOCUMENTS 2,742,585 A * 4/1956 Zemany ..... 313/7
2,795,716 A * 6/1957 Roberts ..... 313/7
2,814,018 A * 11/1957 Zemany ..... 324/468
2,934,694 A * 4/1960 Vacca ..... 324/468
3,076,139 A * 1/1963 Roberts ..... 324/468
3,144,600 A * 8/1964 Roberts ..... 324/468
3,363,451 A * 1/1968 Roberts ..... 73/40.7
3,439,261 A * 4/1969 Loh et al. ..... 324/464
3,439,262 A 4/1969 Roberts
3,471,746 A * 10/1969 Roberts ..... 315/111.91
3,535,088 A * 10/1970 Zimmermann ..... 422/54
3,739,260 A * 6/1973 Schadler ..... 324/468
3,742,475 A 6/1973 Liebermann et al.
3,875,499 A * 4/1975 Roberts ..... 324/468
3,949,390 A 4/1976 Rayl et al.
3,979,625 A 9/1976 Roberts
3,991,360 A 11/1976 Orth et al.
4,053,825 A 10/1977 Young
4,129,418 A 12/1978 Davis
4,151,641 A 5/1979 Mitoff
4,157,311 A 6/1979 Orth et al.
4,196,427 A * 4/1980 Rudberg ..... 340/634
4,203,726 A * 5/1980 Patterson ..... 436/103
4,282,521 A 8/1981 Lieberman
4,488,118 A 12/1984 Jeffers et al.
4,499,054 A * 2/1985 Katsura et al. ..... 422/98
4,524,047 A * 6/1985 Patterson ..... 422/98
4,609,875 A 9/1986 Jeffers
4,666,672 A 5/1987 Miller et al.
4,670,405 A 6/1987 Stetter et al.
RE32,552 E 12/1987 Liebermann et al.
4,744,954 A 5/1988 Campbell et al.
4,771,006 A 9/1988 Miller et al.
4,779,446 A 10/1988 Rowland et al.
4,831,332 A 5/1989 Rudisill et al.
4,839,143 A 6/1989 Vora et al.
4,879,546 A 11/1989 Dunham et al.
4,910,463 A 3/1990 Williams, II et al.
4,929,049 A 5/1990 Le Goullon et al.
5,012,197 A 4/1991 Seiffert et al.
5,104,513 A 4/1992 Lee et al.
5,106,756 A 4/1992 Zaromb
5,115,666 A 5/1992 Williams
5,153,520 A 10/1992 Dumbeck
5,157,333 A 10/1992 Peacock et al.
5,184,500 A 2/1993 Krema et al.
5,198,774 A 3/1993 Williams, II et al.
5,214,412 A 5/1993 Gavlak et al.
5,226,309 A 7/1993 Stetter et al.
5,250,906 A * 10/1993 Bills et al. ..... 324/462
5,260,036 A 11/1993 Weigold
5,284,569 A 2/1994 Lee et al.
5,293,130 A 3/1994 Allman et al.
5,301,537 A 4/1994 Atkinson
5,331,840 A 7/1994 Williams
5,347,223 A 9/1994 Krema et al.
5,351,037 A 9/1994 Martell et al.
5,374,404 A 12/1994 Weigold et al.
5,397,552 A 3/1995 Weigold et al.
5,400,015 A 3/1995 Liebermann
5,444,435 A 8/1995 Williams, II et al.
5,448,905 A 9/1995 Stetter et al.
5,490,413 A 2/1996 Atkinson
5,521,098 A * 5/1996 Hermann et al. ..... 436/149
5,561,065 A 10/1996 Schabron
5,601,184 A 2/1997 Weigold
5,707,595 A 1/1998 Weigold et al.
5,932,176 A 8/1999 Yannopoulos et al.
5,959,191 A 9/1999 Lewis et al.
5,976,883 A 11/1999 Schabron
5,979,054 A 11/1999 Weigold et al.
6,081,121 A * 6/2000 Bills ..... 324/460
6,182,497 B1 * 2/2001 Krajci ..... 73/23.2
6,362,741 B1 * 3/2002 Hickox et al. ..... 340/605
6,644,098 B2 11/2003 Cardinale et al. ..... 73/25.01
6,703,840 B2 3/2004 Cardinale ..... 324/535
7,074,365 B1 7/2006 Shoaf ..... 422/82.08
7,487,662 B2 * 2/2009 Schabron et al. ..... 73/23.2

OTHER PUBLICATIONS

Johnson, M., Analytical Chemistry 1997, 69, 1279–1284.*

Powers, S. E. et al, Ground Water Monitoring & Remediation 1997, 17, 130–140.*

Stenger, V. A. et al, Industrial and Engineering Chemistry Analytical Edition 1939, 11, 121–124.*

Schultz, H. A., Analytical Chemistry 1957, 29, 1840–1842.*

Gobrecht, H. et al, Fresenius' Journal of Analytical Chemistry, 1964, 199, 81–88.*

Braman, R. S. et al, Analytical chemistry 1968, 40, 95–106.*

Stetter, J. R. et al, Analytical Chemistry 1990, 62, 182–185.*

"TID—Thermionic Ionization Detector" http://www.schambeck–sfd.com/GC__en/gc__TID.htm. Downloaded and printed on Sep. 4, 2003. 3 pages.

"Chemical Agents," Chemical and Biological Terrorism, National Academy Press, National Research Counsel, 1999, p. 113–131.

"Detection and Measurement of Chemical Agents," Chemical and Biological Terrorism, National Academy Press, National Research Counsel, 1999, p. 43–65 and 227–263.

Adams, J.W., et al., 1967, "Development of Cone Penetrometer Electrochemical Sensor Probes for Chlorinated Solvents and Explosives," Field Analytical Methods for Hazardous Wastes and Toxic Chemicals, Air & Waste Management Assn, pp. 667–670.

Baron, Dirk, "Science 360B–Introductinto Hydrologic Systems." Dr. Dirk Baron, printed Dec. 11, 2002, 3 pages, http://www.cs.csubak.edu/Geology/Faculty/Baron/SuppGWNotes–5.html.

Buttner, WIJ., et al., 1995, "A Hand–Portable Instrument System for Real–Time Analysis of Chlorinated Organic Compound Contamination," Field Screening Methods for Hazardous Wastes and Toxin Chemicals, vol. 2, Air & Waste Management Assn, pp. 702–712.

Ewing, K.J., et al., 1995, "Fiber Optic Raman Volatile Organic Compound Sensor," Field Screening Methods for Hazardous Wastes and Toxic Chemicals, vol. 1, Air & Waste Management Assn, pp. 364–371.

Frye, G.C., et al., 1995, "Above–Ground In–Situ Field Screening of VOCs Using a Portable Acoustic Wave Sensor (PAWS)," Field Screening Methods for Hazardous Wastes and Toxic Chemicals, vol. 2, Air & Waste Management Assn., pp. 715–726.

Haas, J.W., et al., 1995, Nonaqueous Phase Liquids: Searching for the Needle in the Haystack,: Field Screening Methods for Hazardous Wastes and Toxic Chemicals, vol. 1, Air & Waste Management Assn., pp. 443–449.

Hewitt, A.D. and Lukash, N.J., 1997, "Rapid Method for Estimating the Total Concentration of Volatile Organic Compounds in Soil Samples," Field Screening Methods for Hazardous Wastes and Toxic Chemicals, Air & Waste Management Assn., Pittsburgh, PA.

Hudak, R., Melby, J., Onisk, D., and Stave, J., 1995, "Validation of an Immunoassay Field Screen for Trichioroethylene (TCE)," Field Screening Methods for Hazardous Wastes and Toxic Chemicals, vol. 1, pp. 101–108, Conference Proceedings, Air & Waste Management Assn., Pittsburgh, PA.

Linenberg, A., 1995, "On–Site Monitoring of Vinyl Chloride at Part Per Trillion Levels in Air," Field Screening Methods for Hazardous Wastes and Toxic Chemicals, vol. 1, Air & Waste Management Assn., pp. 236–245.

Myers, K.F., et al., 1995, "Laboratory Evaluation of a Volatile Organic Compound Analysis System for the Site Characterization and Analysis Demonstration System," Field Screening Methods for Hazardous Wastes and Toxic Chemicals, vol. 1, Air & Waste Management Assn., pp. 177–184.

Penrose, William, 1993, "Chlorinated hydrocarbon vapor sensor technologies include PID, FID, helium plasma arc, solid state sensor," EPA, pp. 3.

Plumb, Jr., R.H., 1992, "The Importance of Volatile Organic Compounds as a Disposal Site Monitoring Parameter," in Lesage, S. and R.E. Jackson, eds., "Groundwater Contamination and Analysis of Hazardous Waste Sites," Marcel Dekker, New York, NY, pp. 173–197.

Rossabi, J., et al., 1993, "In Situ, Subsurface Monitoring of Vapor–Phase TCE using Fiber Optics," Proceedings of the 1993 USEPA/A&WMA, Internat'l Symposium on Field Screening Methods for Hazardous Wastes and Toxic Chemicals, Air & Waste Management Assn., pp. 1165–1175.

Schabron, J.F. and Rovani, Jr., J.F., 1997, "Practical Deviations from Henry's Law for Water/Air partitioning of Volatile Organic Compounds," Proceedings of the 1997 USEPA/A&WA Internat'l Symposium on Field Screening Methods for Hazardous Wastes and Toxic Chemicals, Air & Waste Management Assn., pp. 417–426.

Schabron J.F., et al., 1996, Down Hole Photoionization Detection of Volatile Organic Stach; Flachowsky, J. Brodacki, M and Doring, HIRI, 1995, "Field Screening for Volatile Organochlorine Using Ion Mobility Spectrometry," Field Screening Methods for Hazardous Wastes and Toxic Chemicals, vol. 2, Air & Waste Management Assn., pp. 1046–1050.

"Refrigerant Leak Detectors," TIF Instruments, Inc., 1 page.

"Leak Detectors," TIF Instruments, Inc., Oct. 29, 2001, 1 page.

Walt, D.R., 1998, "Fiber Optic Imaging Sensors, Accounts of Chemical Research," 31, pp. 267–278.

"Refrigerant Leak Detector," Yokogawa Corporation of America, 1 page.

"Refrigerant Monitor Specifications," Yokogawa Corporation of America, 2000, 1 page.

Stach, J., J. Flachowsky, M. Brodacki, and H.R. Doring, 1995, Field Screening for Volatile Organochlorine Compounds Using Ion Mobility Spectrometry, Field Screening Methods for Hazardous Wastes and Toxic Chemicals, vol. 2, Air & Waste Management Association, pp. 1046–1050.

TIF Instruments, Inc. "Refrigerant Leak Detectors", 1 page.

TIF Instruments, Inc. Oct. 29, 2001, "Leak Detectors", 1 page.

Yokogawa Corporation of America, "Refrigerant Leak Detector", 1 page.

Yokogawa Corporation of America, 2000, "Refrigerant Monitor Specification", 1 page.

U.S. Nonprovisional "Soil Extractions Stirring System", U.S. Appl. No. 09/558,979, filed Apr. 27, 2000, 20 pages and 3 drawings.

U.S. Appl. No. 60/340,561, filed Dec. 13, 2001, entitled "Halogenated Volatile Organic Compound Screening and Measurement", 18 pages and 1 drawing.

U.S. Appl. No. 60/405,638, filed Aug. 23, 2002 entitled "System To Selectively Detect The Presence Of Chemical Warfare Agents", 12 pages and 2 drawings.

International Preliminary Examination Report, PCT/US02/40082, Sep. 28, 2004, 5 pages.

* cited by examiner

GA Tabun
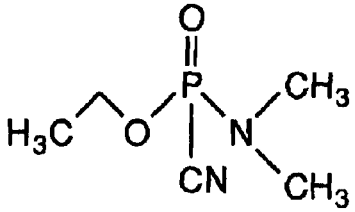
GB Sarin
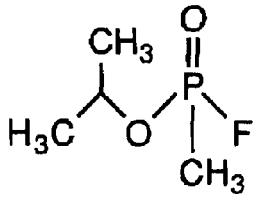
GD Soman
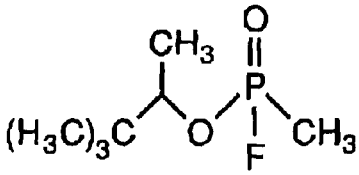
VX
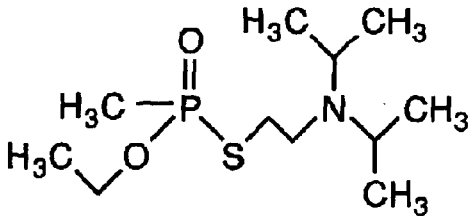
Figure 25
AC Hydrogen Cyanide
HCN
CK Cyanogen Chloride
CNCl
Figure 26

Chlorine

$Cl_2$

CG Phosgene

HD Sulfur Mustard

Nitrogen Mustard

Lewisite

$Cl-CH=CH-AsCl_2$
(cis-and trans)

SARIN

PHOSGENE

SULFUR MUSTARD

VOLATILE ORGANIC COMPOUND SENSOR SYSTEM

Matter enclosed in heavy brackets [ ] appears in the original patent but forms no part of this reissue specification; matter printed in italics indicates the additions made by reissue.

CROSS-REFERENCES TO RELATED APPLICATIONS

This application claims the benefit of U.S. Provisional Application No. 60/340,561, filed Dec. 13, 2001, entitled "Halogenated Volatile Organic Compound Screening and Measurement" and U.S. Provisional Application No. 60/405,638; filed Aug. 23, 2002 entitled "System To Selectively Detect The Presence Of Chemical Warfare Agents", both hereby incorporated by reference.

ACKNOWLEDGMENT OF GOVERNMENT SUPPORT

This invention was made with federal government support under Cooperative Agreement Nos. DE-FC26-98FT40322 awarded by the U.S. Department of Energy. The federal government may have certain rights in this invention.

TECHNICAL FIELD

Generally, this invention relates to the development of field screening methodology for new substances and sensing chemical warfare agents (CWAs) and terrorist substances. It also relates to a portable test kit which may be utilized to measure concentrations of halogenated volatile organic compounds (VOCs) in the field. Specifically it relates to systems for reliably field sensing the potential presence of such items while also distinguishing them from other elements potentially present. It also relates to overall systems and processes for sensing, reacting, and responding to an indicated presence of such substances.

BACKGROUND

Contamination by halogenated volatile organic compounds (VOCs) may be considered to be a widespread problem at U.S. Department of Energy (DOE) and military sites. It also has environmental ramifications. Compounds such as carbon tetrachloride, trichloroethylene, tetrachloroethylene, etc. may commonly be referred to as dense nonaqueous phase liquids (DNAPLs). These compounds may have been used extensively in degreasing and equipment cleaning operations in the past, with disposal practices that led to their release into the ground, and thus may be considered the most significant organic contaminants in groundwater associated with disposal sites (Plumb 1992).

For measurement of concentrations or amounts, the photoionizaton detector (PID) may be among the most common VOC field measurement tool in use today. A typical PID lamp energy may be 10.6 electron volts (eV), which can be sufficient for ionizing compounds containing double bonds. However, halogenated compounds without double bonds such as carbon tetrachloride or methylene chloride may require an energy of 11.7 eV for ionization (Table 5) (Schabron et al. 1996). This may only be accomplished with a PID equipped with a lithium fluoride window, which may be considered to have a short lifetime due to the solubility of lithium fluoride in water. Also, a PID may not be considered to be selective for halogenated compounds. Many other compound types may be detected also. Field screening of soils with a PID probe may involve placing a soil sample in a plastic bag or a glass jar, sealing the bag or covering the jar with aluminum foil, then inserting the PID probe tip through the foil (Hewitt and Lukash 1997).

In an unrelated field, leak testing of refrigerants is often conducted in situations warranting isolated testing events. In such situations, heated diode and corona discharge sensors are used merely as alarm sensors to detect leaks of refrigerants from air conditioners, freezers, and refrigerators, since both heated diode and corona discharge sensors are selective to the presence of halogens or carbon-halogen bonds. These test procedures, however, have been viewed as not applicable to quantitative analysis.

In situations calling for quantitative analysis of VOCs, PID's are used. Besides the aforementioned problems, though, such hand-held PID detectors may also suffer from the disadvantage in that they may not be able to discriminate between halogenated and non-halogenated species (Table 5). A more detailed analysis which may also allow for some speciation involves a portable gas chromatograph (Myers et al. 1995, Linenberg 1995). This is a relatively expensive type of device, however, skilled operators are usually required, as is the flow of a chemically inert carrier gas. Immunoassay kits may also allow for rapid field analysis (Hudak et al. 1995). This approach may require temperature control and critical timing for the several steps involved.

Several novel approaches have been proposed for surface or down-hole screening of halogenated VOCs in the field. One approach may use refractive index attenuation on coated optical fibers (Le Goullon and Goswami 1990). Another technology may utilize a chemical reaction in a basic media to form a color in the presence of trichloroethylene (Rossabi et al. 1993). Yet, another probe may use a heated $LaF_2$ doped element heated to 600° C. to measure volatile chlorine containing compounds (Buttner et al. 1995). A synthetic nose consisting of an array of different chemicals which may give different optical response to various volatile analytes has been proposed (Walt 1998). Other approaches may also include Raman spectroscopy (Ewing et al. 1995, Haas et al. 1995), electrochemical cells (Adams et al. 1997), acoustic wave devices (Frye et al. 1995), and ion mobility spectrometry (Stach et al. 1995). The above devices certainly may all contribute some progress towards the problem of monitoring for some of the VOC indicator compounds at various levels, but none meet user needs across the full spectrum.

Thus, there exists a need for a new type of simple field monitor (such as a portable field kit) which is selective to halogenated VOCs, field-worthy (portable, not overly complex to operate, not requiring extensive (or perhaps any) on-site lab facilities, and enabling field monitoring, including in situ sensing or operating of the monitor), and does not require skilled operation (meaning it is easy to operate by anyone with only minimal instruction). HVC (halogenated volatile compound) sensing (or more generally sense operating) upon merely positioning a sensor in an area of interest an activating a switch(es) is a desirable feature. Sensing as used herein may refer to sensing for the presence of a chemical and/or determining the concentration of a chemical. Monitoring may be characterized by any type of chemical group (halogenated VC, e.g), or by purpose (environmental, groundwater, or soil, as but a few examples). Monitoring includes sensing to assess the presence of a chemical functional group and/or sensing to determine the concentration of a chemical functional group.

The presence of chemical warfare agents (CWAs) and terrorist substances is one of increasing concern. Hand-held and portable sensor systems are commercially available for the detection of various chemicals in vapor form in ambient air. These sensors typically use a detector system based on photoionization, corona-discharge, heated diode, thermal conductivity, ion mobility spectrometry, ion capture, or other technology. Many of the sensor systems incorporate an air pump to flow sampled air past the detector, while other sensors use air diffusion. Generally, they do not, however, offer adequate differentiation to be employed in the highly sensitive security setting. For example, if only a halogen-selective detector device were used for the detection of halogen-containing chemical warfare agents (CWAs) such as sarin, soman, phosgene, and sulfur mustard, the inability to differentiate between these chemicals and other more common chemicals such as refrigerants, dry cleaning solvents, and degreasing solvents might cause a false alarm in a public setting. This could cause panic and hysteria.

Current state-of-the-art sensor technology suffers to some degree from a lack of applicability of individual sensors to a variety of chemical vapors. Often, individual detector systems are either too specific or too broad in scope for measuring a suite of chemical vapors. A detector that is too specific, such as corona-discharge, is limited to detection of a unique chemical structure and cannot evaluate chemicals of different classes. A detector that is too broad-based, such as thermal conductivity, responds to almost any vapor without regards to chemical specificity. Systems capable of identifying individual compounds, such as mass spectrometers, can often be too expensive for widespread deployment.

DISCLOSURE OF INVENTION

An important aspect of the initial data collection for the present invention includes the use of commercially available heated diode and corona discharge leak detectors which can be obtained from the manufacturers and modified or utilized as necessary to provide a signal related to VOC concentration. In addition, efforts may include the evaluation and potential calibration of sensor response using carbon tetrachloride and tetrachloroethylene (perchloroethylene, PCE) since these compounds represent halogenated VOCs, with and without double bonds. Using this approach, the response characteristics may be determined for the VOCs directly in headspace in Tedlar bag containers. Quantitation limits for carbon tetrachloride in the air were estimated to be 1 ug/L (0.2 ppmv) by using the modified heated diode detector and 50 ug/L (10 ppmv) by using the modified corona discharge detector. Detector operation was not modified to provide additional sensitivity although this could be possible as well. An operative sensitivity might be improved if a signal to noise ration is improved by minimizing the size of the apparatus, and/or by arranging the apparatus in a sensor array that includes at least one additional halogenated volatile compound sensor apparatus (perhaps forming a parallel sensor array), as but two examples. Potential interferences from volatile hydrocarbons, such as toluene, heptane, and the like were also evaluated. In one embodiment these interferences may be concluded as not significantly affecting the response from either such detector. Another important aspect of the detection process may be the effect of humidity. The heated diode detector may not respond significantly to humidity while the corona discharge detector may give a slight response to humidity, which may then be zeroed out as background. The results of these efforts indicate the value that both devices may have for analytical method development work toward one goal of the present invention of developing a portable test kit for screening and measuring halogenated VOCs in the field. These results may also suggest the use of the sensors in the present invention to merely detect the presence of halogen-containing volatile chemical warfare agents (or halogenated volatile compound chemical warfare agent, which may be a halogenated volatile organic compound chemical warfare agent) in air at low levels. Halogen-containing chemical warfare agents include sarin, phosgene, and mustard gas, etc., (see FIG. 28).

One embodiment of the present invention may be a field portable kit based on heated diode or corona discharge monitor technology for screening for halogenated VOCs in the field. Another embodiment may be the application of this technology to quantitative analysis. Of commercial importance is the fact that two widely used commercially available refrigerant leak detectors can be modified and used as both field screening and monitoring devices for new types of halogenated VOCs and as a quantitative tool. Indeed, the objectives of the present invention include using commercially available refrigerant leak detectors as continuously operable field screening and monitoring devices and as measurement devices.

Heated diode leak monitors were manufactured by Yokogawa and now by Bacharac, Inc., Newnan, Ga. These operate on 12 volts at less than 1 amp. Corona discharge leak monitors are commercially available from American Test Products Inc., Mirimar, Fla. These are the so-called TIF sensors may involve high impedance circuits operating at about 1,600 volts at the detector tip. Both types of sensor systems are said to be capable of detecting leaks of down to approximately 0.1 to 0.5 ounce of refrigerant per year. Both of these detectors are sold as alarm monitors without a quantitative or a digital readout. In one embodiment, the present invention may involve modification of these types of commercially available heated diode and corona discharge monitors to provide quantitative or semi-quantitative determination and display (digital readout or otherwise, steady-signal readout or otherwise) of halogenated VOCs in the field. Other monitors, commercially available or not, that also are responsive to halogens or carbon-halogen bonds may also be modified to sense in the field the presence of halogenated VOCs in a manner similar to that described herein. Results to date suggest the possibility of using the above-specified (and other) sensors to detect halogen-containing volatile chemical warfare agents in air at low levels. Additional initial experiments performed with carbon tetrachloride and tetrachloroethylene in air and soil may provide a method by which to define product specification and establish the concept discussed in the present invention which may then assist in creating the new analytical methods of detection.

In one embodiment, the present invention involves field test kits and the measurement of VOCs and may be an important aspect in developing new environmental monitoring applications for heated diode or corona discharge-based leak detectors, and the like, and for selectively screening for new substances or measuring new and more traditional halogenated VOCs in the field. The devices could perhaps be used with the plastic bag or aluminum foil covered jar sampling method described above for soil samples; they may involve utilization of the headspace above a contained water. Such use may involve water sparging to rapidly release volatile organic compounds entrained or dissolved in the water (which includes freshwater, seawater, brackish water, groundwater, as but a few different types). Alternatively, the devices could be used as a portable cost effective means of detecting volatile halogen-containing chemical warfare agents such as sarin, phosgene, mustard gas, or chlorine, and the like in air. The XP-1 has an air fan in the body of the unit, but it does not work well. Another important inventive aspect of the system involves retrofitting onto a corona discharge sensor a pump that provides a controlled and variable flow of air across the sensor and enhances sensitivity, accuracy and field operability of the device or apparatus.

Yet another important aspect of another embodiment of the present invention may involve the impact of the partitioning of VOCs between air and water as a function of temperature and the concentration of VOC species in water (Schabron et al. 1996, Schabron and Rovani 1997). Headspace may be either in the air above the water table in a well, or a headspace artificially created below the surface of the water by a membrane or other device. An important aspect in the principles of operation for a headspace device may be attributed to Henry's law, which states that the partial pressure $P_i$, or concentration of a volatile component in the headspace is proportional to its concentration in the aqueous solution $C_i$:

$$P_i = H_i \times C_i$$

where $H_i$ is the Henry's law constant for component i. The assumptions in using this approach for determining VOCs are that they have not exceeded their solubility in water, and that they partition into the headspace according to Henry's law. For example, $H_i$ relates the mg/L vapor parts per million (ppmv) level in the headspace to the mg/L concentration in water. Thus, the vapor concentration of toluene in equilibrium with a 1 mg/L aqueous toluene solution at 25° C.(77° F.) is 69 ppmv. By measuring the ppmv levels of volatile organics in the headspace above aqueous solutions of these materials, field screening personnel often assume that the aqueous level can be established. $H_i$ is only defined at infinite dilution. The actual partitioning may vary significantly with total VOC concentration in the water and with temperature. Headspace may only be used to estimate water concentration if the appropriate corrections are made.

The present invention may be expected to support the development of many new commercial products which may provide a cost-effective means to rapidly screen for halogenated VOCs or chemical warfare agents in the field. An important aspect of the present invention involves taking existing refrigerant detector alarm monitors, and with slight hardware modification and comprehensive analytical method development work launching them into a new commercial application with significant utility to the environmental industry. In spite of the availability of such devices, this new use is inventive, as is the method of application associated with this new use, because such uses were often viewed as impossible by those in the field. An important and ultimate goal of the present invention is to develop a field portable kit based on heated diode or corona discharge monitor technology that may be used to screen for halogenated VOCs or chemical warfare agents in the field. Such measurement or screening may be enhanced by the present invention's modification of available halogenated VOC sensors to provide numerical or digital readout indicative of presence or concentrations of halogenated VOCs.

Another important aspect of the present invention is that the detector system be able to work in an environment of varying and often high relative humidity. Response characteristics and background levels may be derived experimentally at different relative humidities. Potential interferences from aliphatic or aromatic hydrocarbons may be considered minimal. The detector even demonstrates a significant selectivity to halogenated VOCs in the presence of non-halogenated VOCs.

BRIEF DESCRIPTION OF THE DRAWINGS

FIG. 25 is Nerve Agents

FIG. 26 is Blood Agents

MODES FOR CARRYING OUT THE INVENTION

Figure 1:
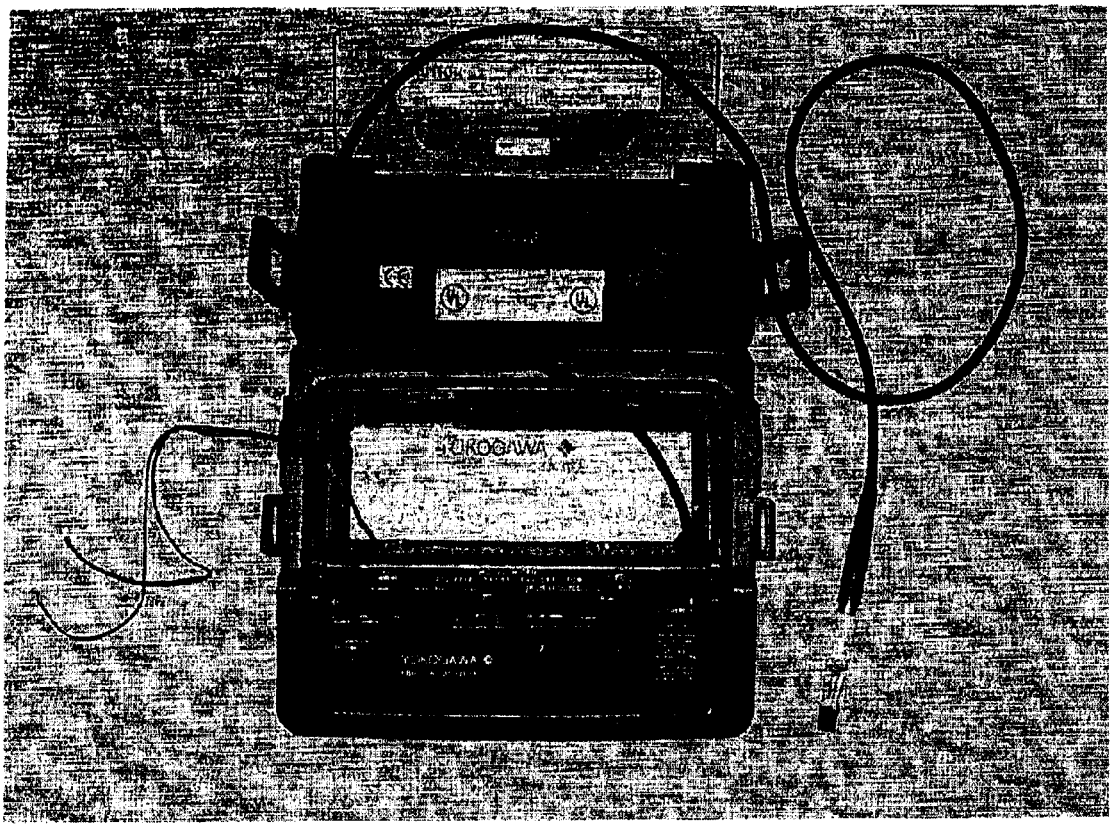
FIG. 1 shows a Yokogawa H-10PM Heated Diode Leak Detector.
Figure 2:
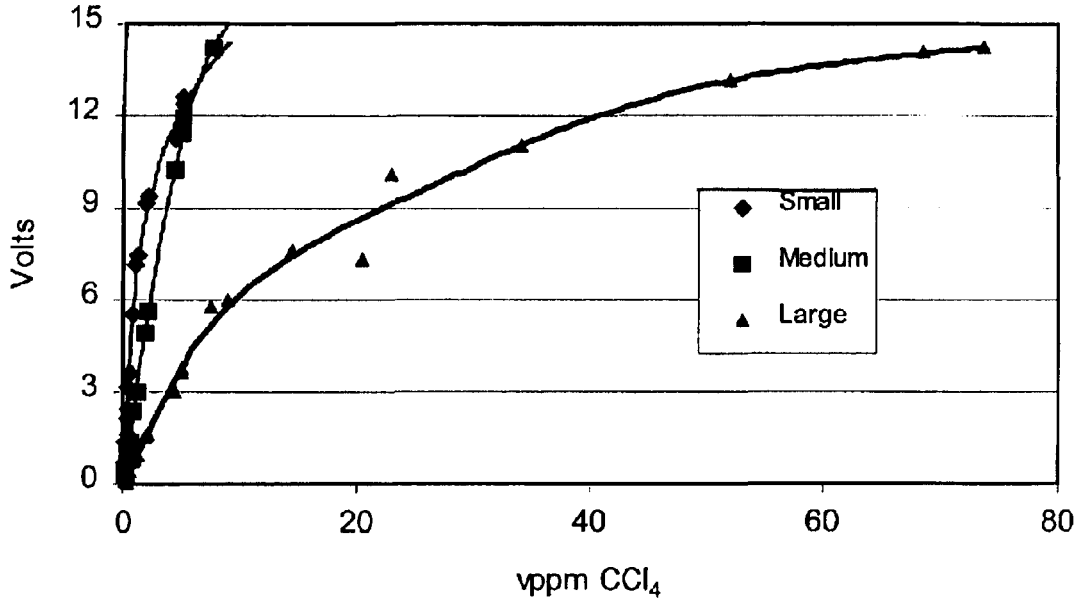
FIG. 2 is a Response Profile of Yokogawa H-10PM
Figure 3:
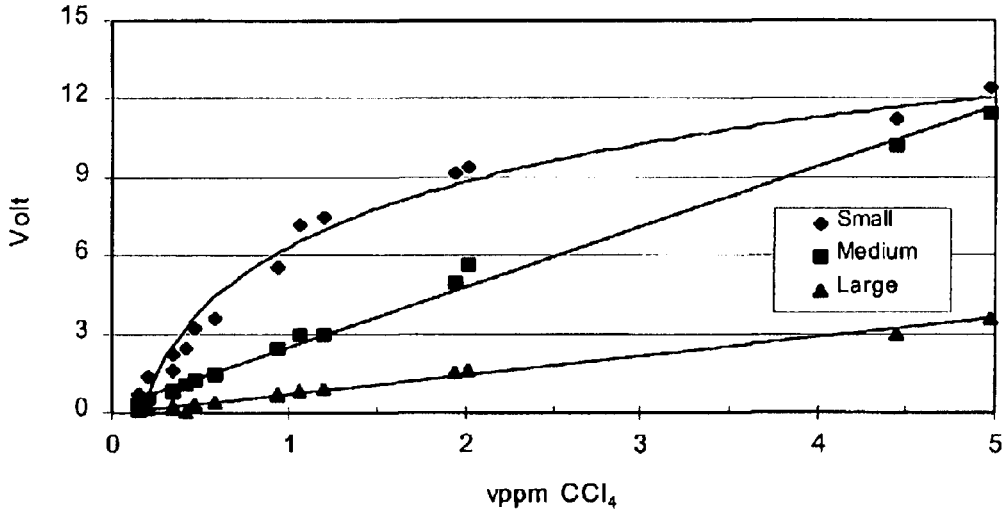
Figure 4:
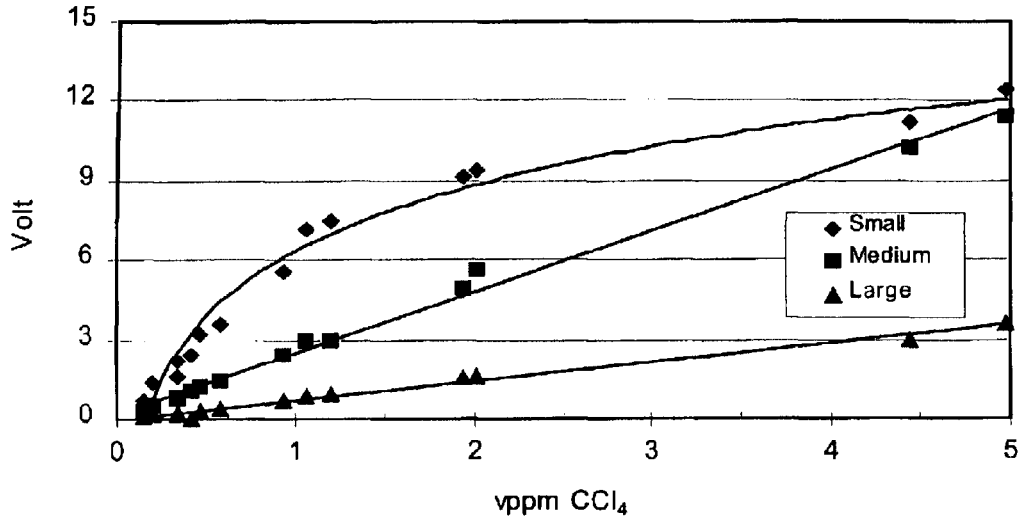
FIG. 4 is a Yokogawa H-10PM Response Profile in Saturated Water Vapor Environment
Figure 5:
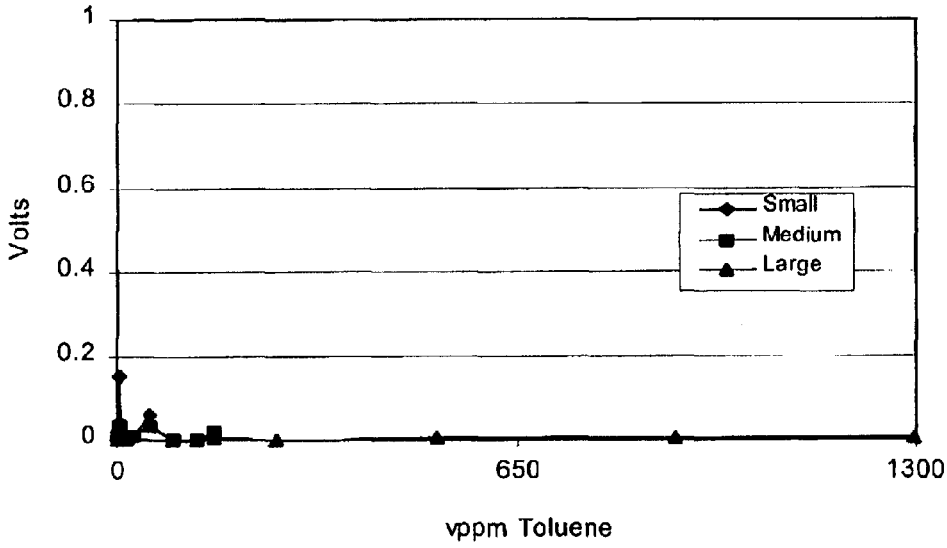
FIG. 5 is a Yokogawa H-10PM Response to Toluene Vapor
Figure 6:
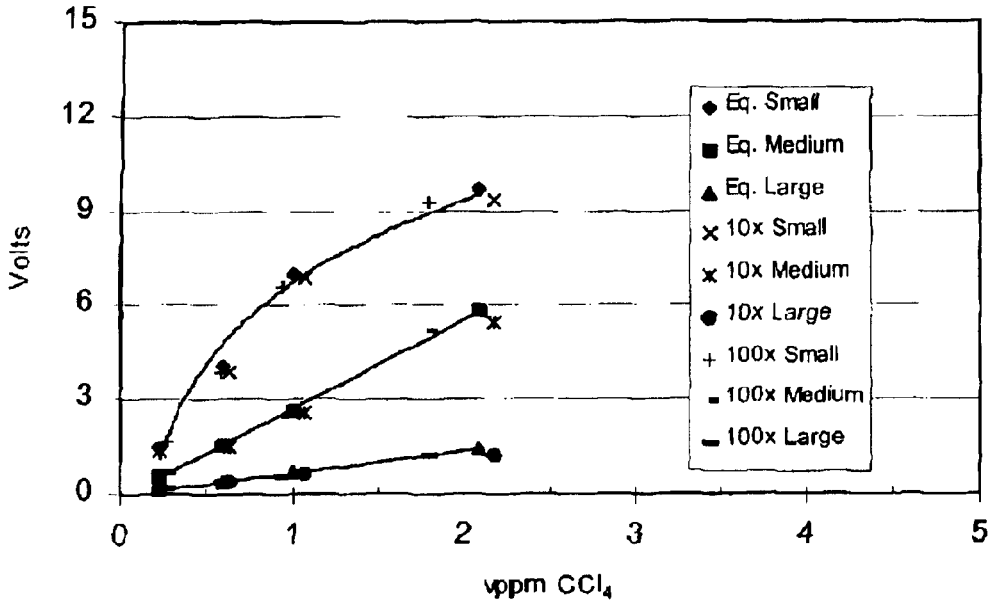
FIG. 6 is a Yokogawa H-10PM Response Profile in Toluene Vapor Environment
Figure 7:
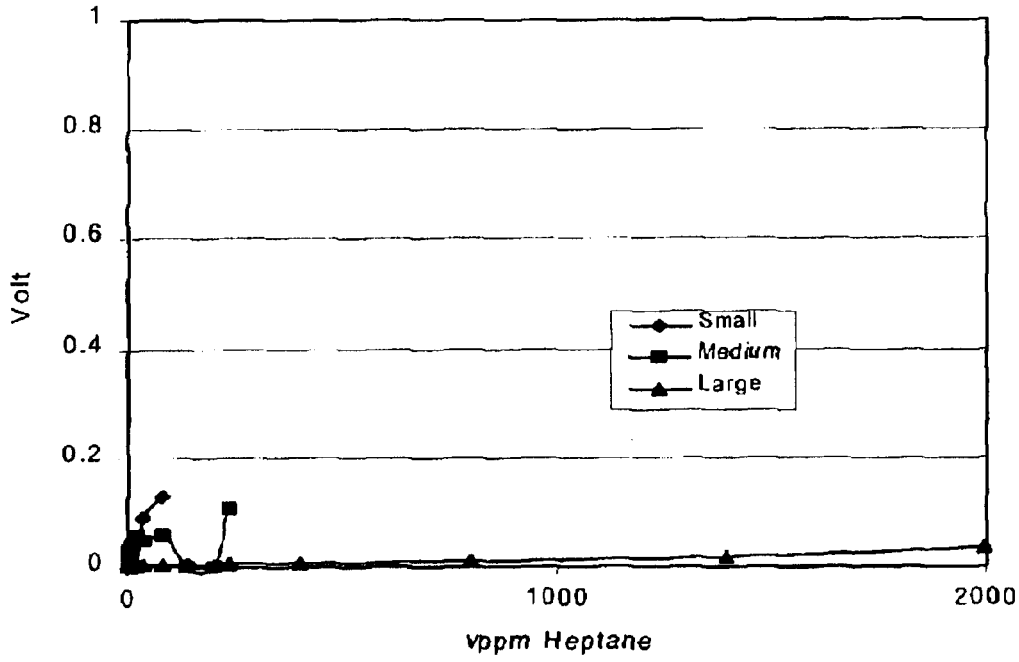
FIG. 7 shows a Yokogawa H-10PM Response to n-Heptane Vapor.
Figure 8:
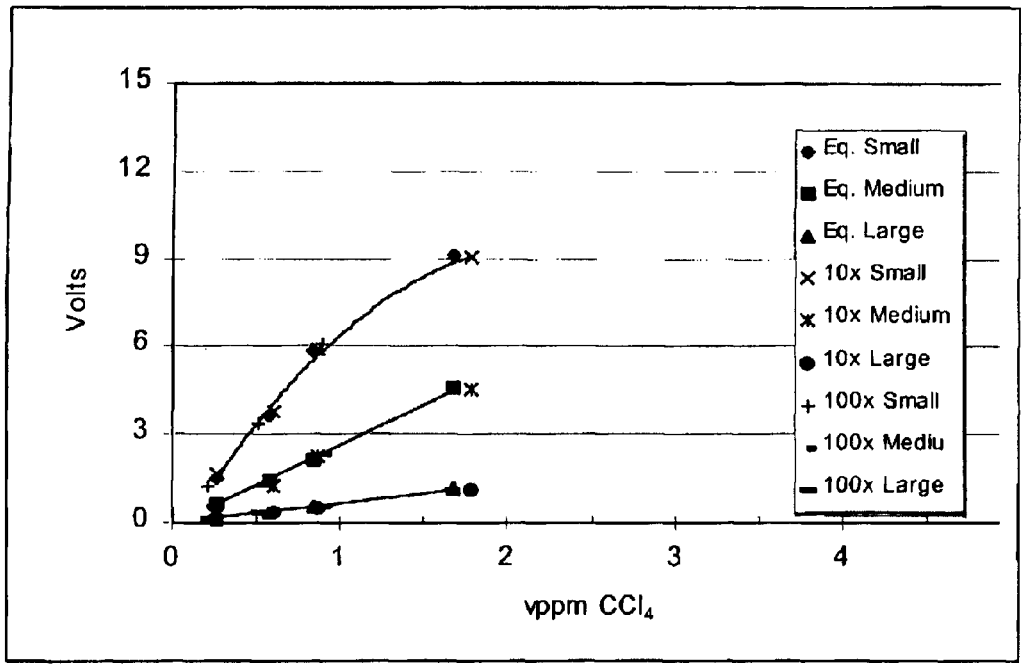
FIG. 8 is a Yokogawa H-10PM Response in n-Heptane Vapor Environment
Figure 9:
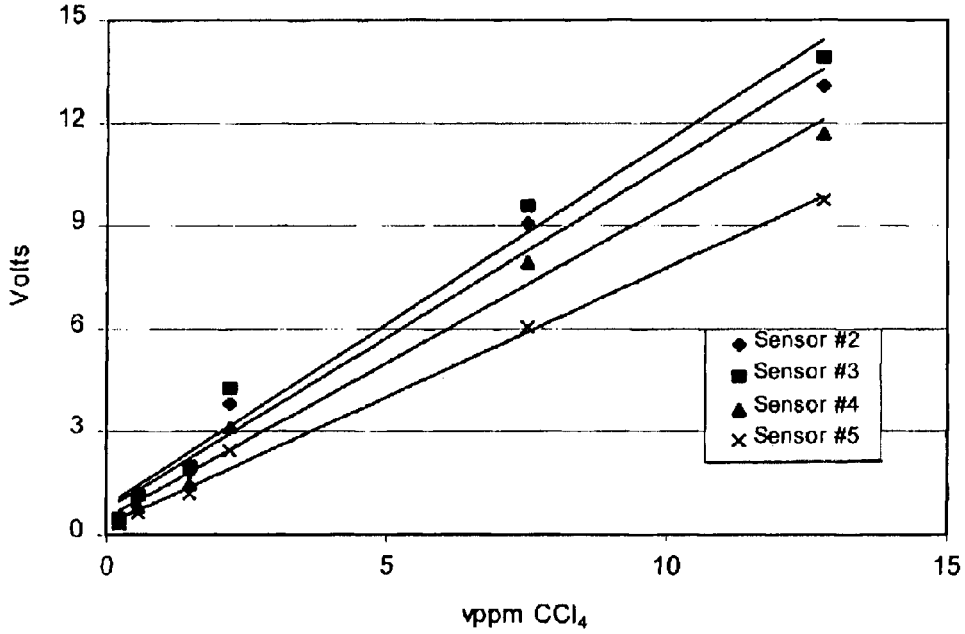
FIG. 9 is a Yokogawa H-10PM Sensor Interchangeability
Figure 10:
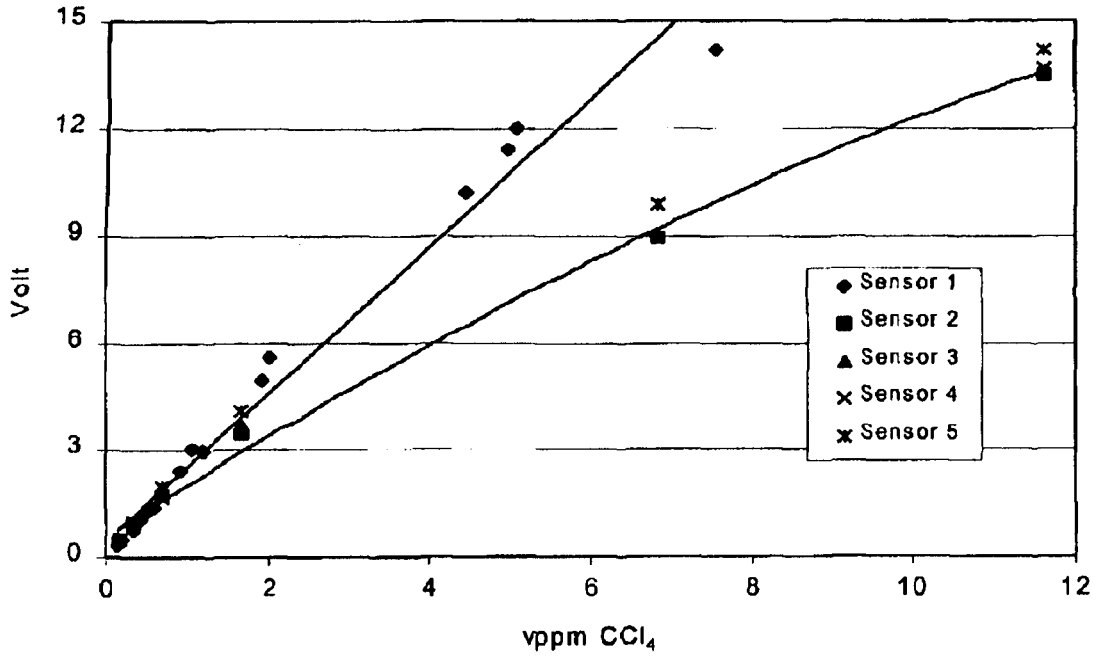
FIG. 10 is a Yokogawa H-10PM Sensor Comparison with Temperature Adjustment
Figure 11:
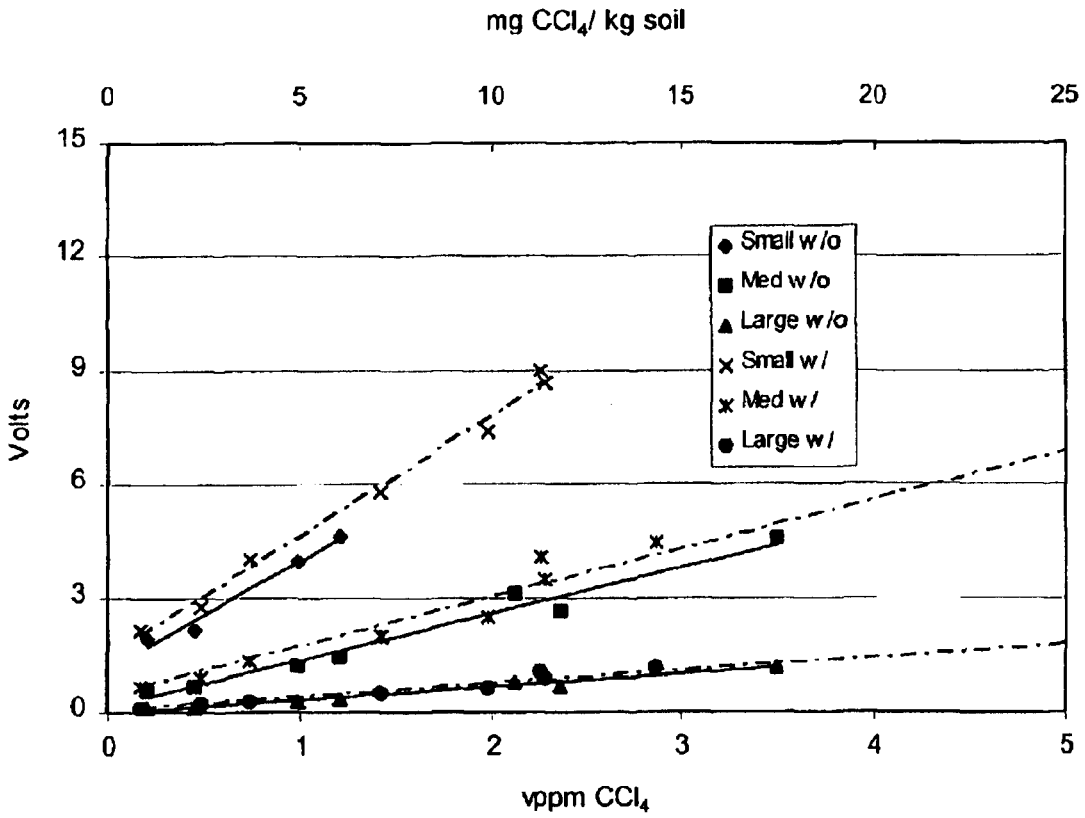
FIG. 11 is a Yokogawa H-10PM Soil Spiking Results
Figure 12:
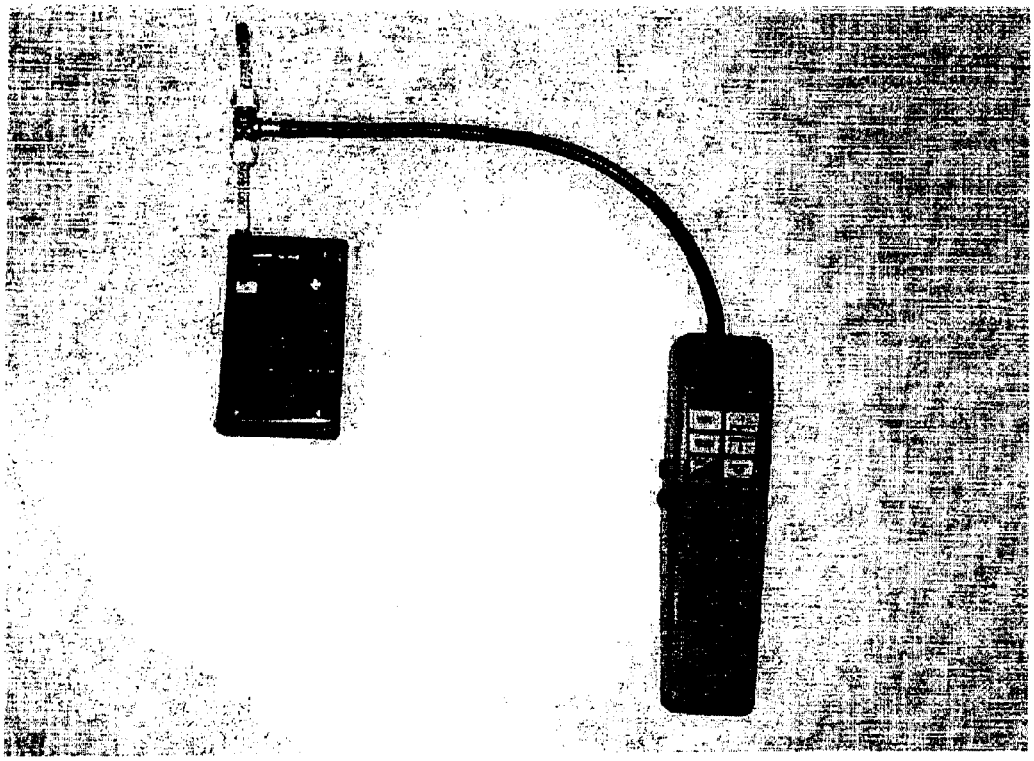
FIG. 12 is a TIF XP-1 Leak Detector with Auxiliary Du Pont P200A Personal Sampling Pump
Figure 13:
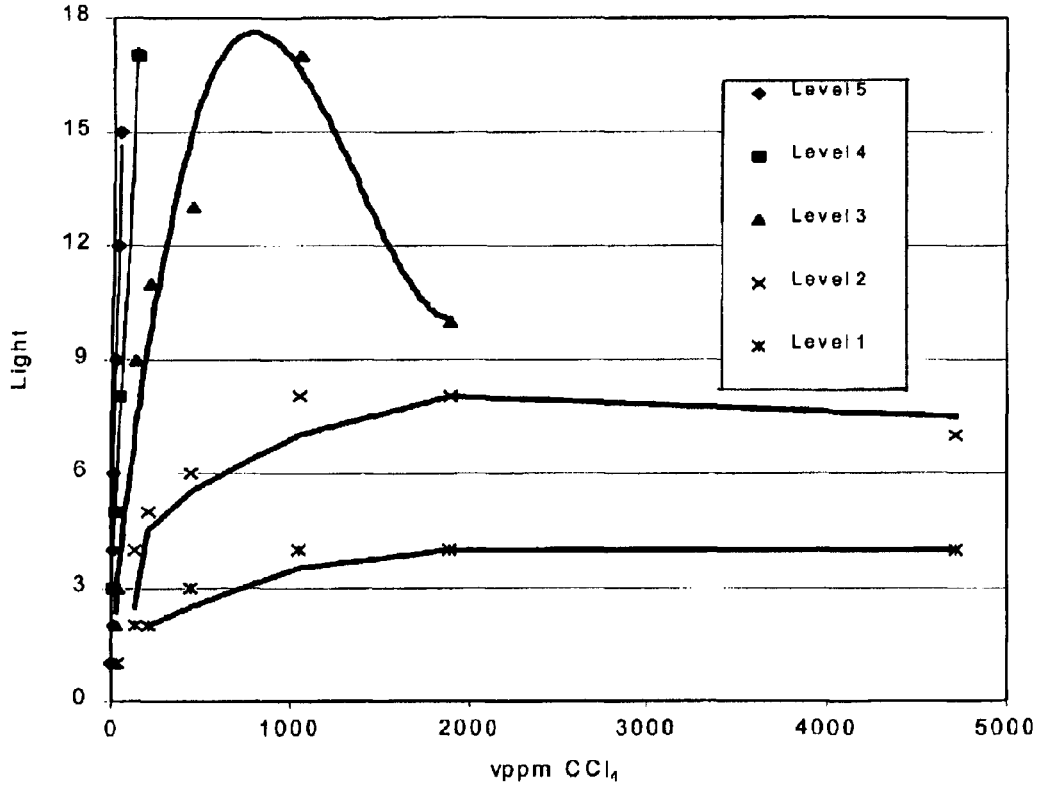
FIG. 13 is a Response Profile of TIF XP-1
Figure 14:
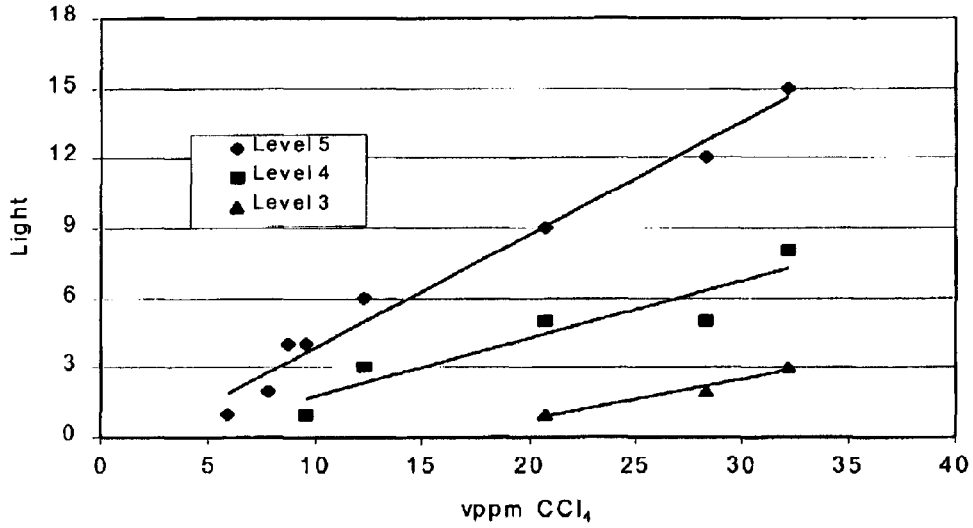
FIG. 14 is a Expanded View of Lower Working Range of TIF XP-1
Figure 15:
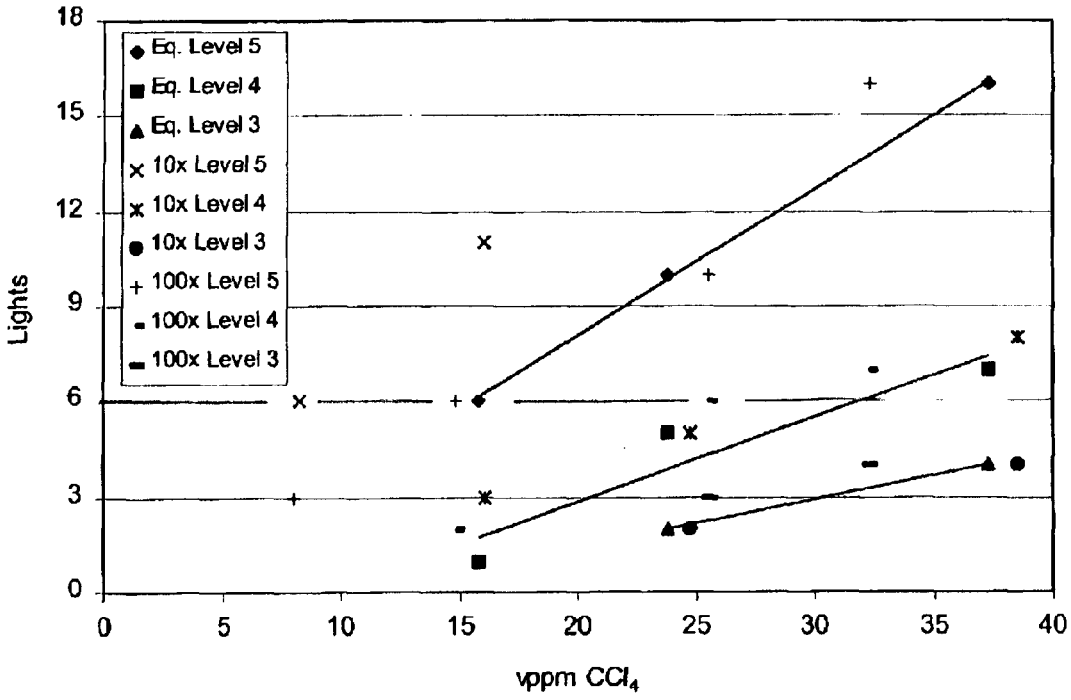
FIG. 15 is a TIF XP-1 Response in Saturated Water Vapor Environment
Figure 16:
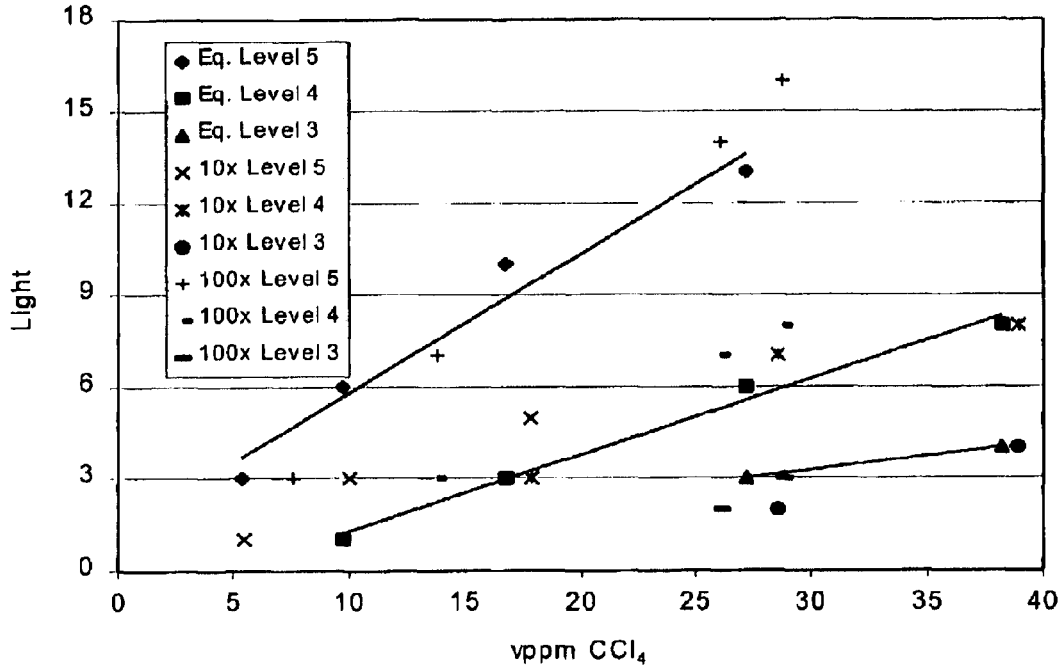
FIG. 16 is a TIF XP-1 Response in Toluene Vapor Environment
Figure 17:
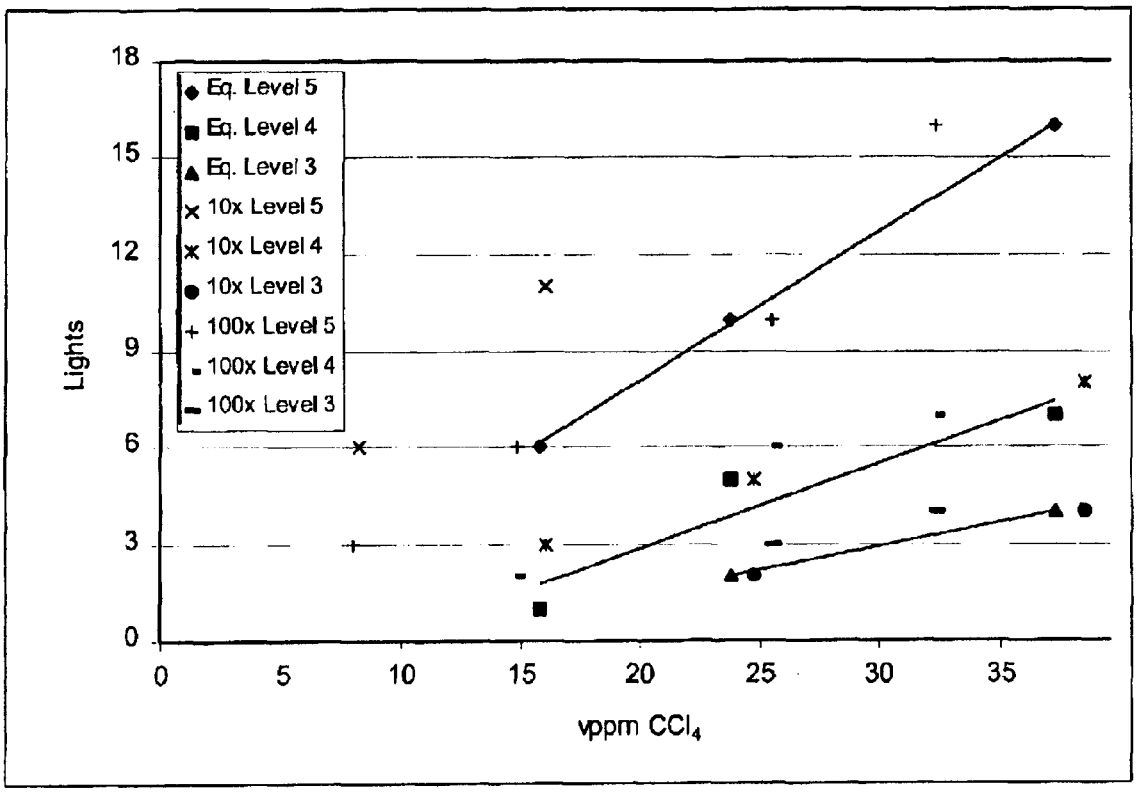
FIG. 17 is a TIF XP-1 Response Profile in n-Heptane Vapor Environment
Figure 18:
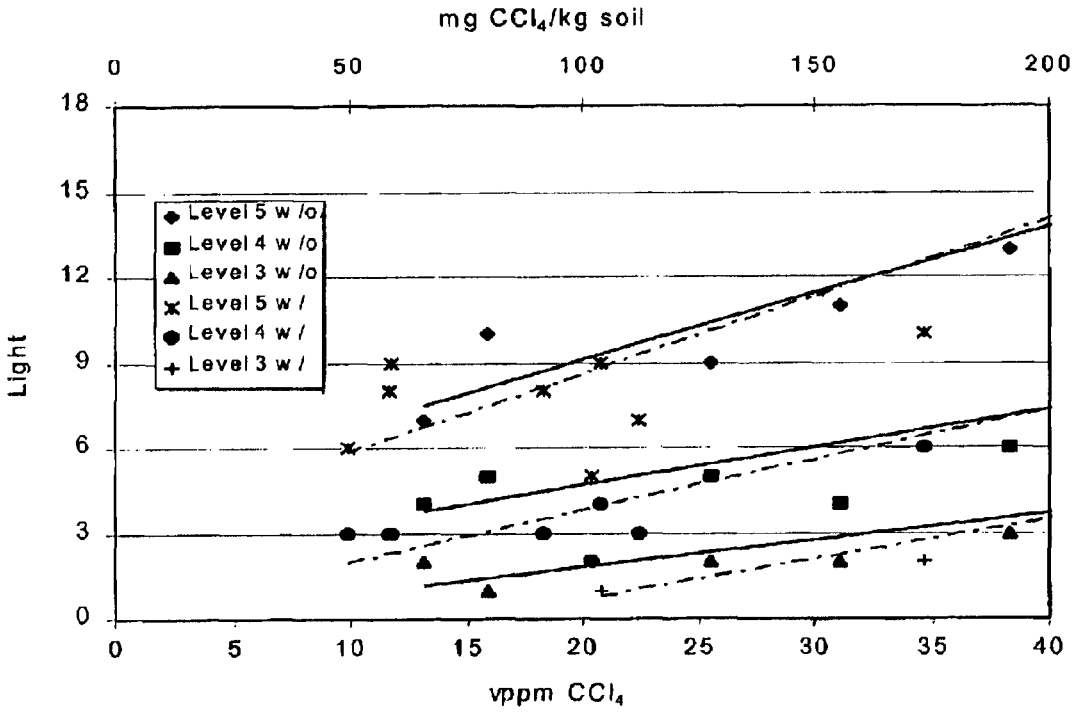
FIG. 18 shows TIF XP-1 Soil Spiking Results.
Figure 19:
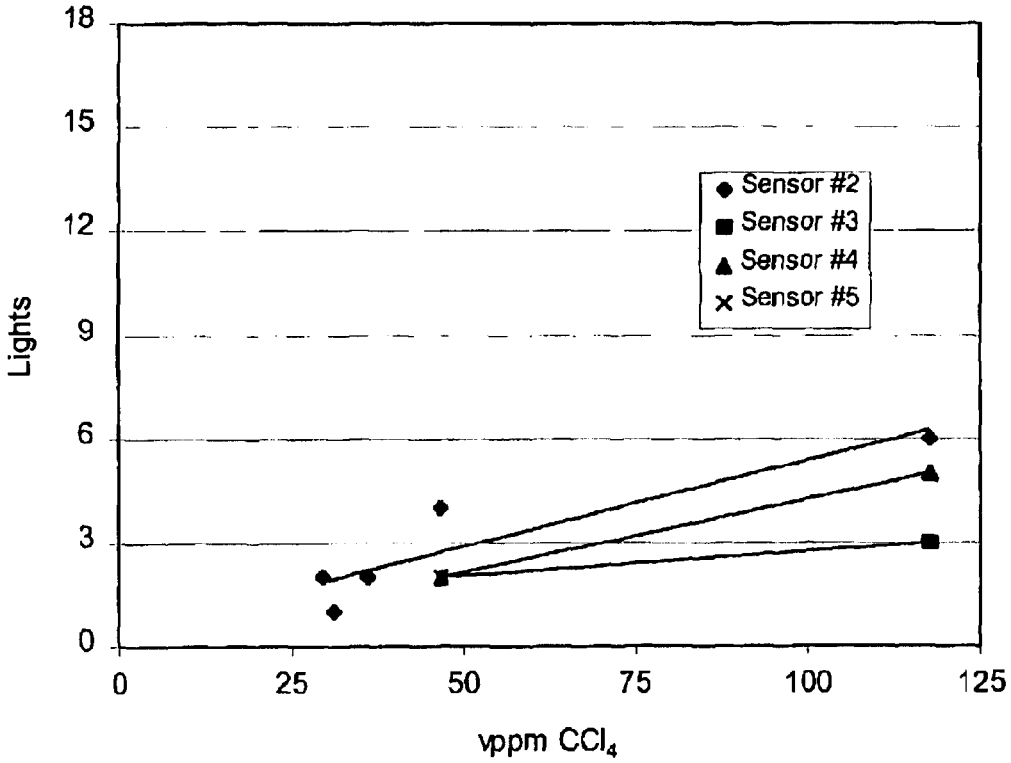
FIG. 19 is a TIF XP-1 Sensitivity Level 3, Sensor Interchangeability
Figure 20:
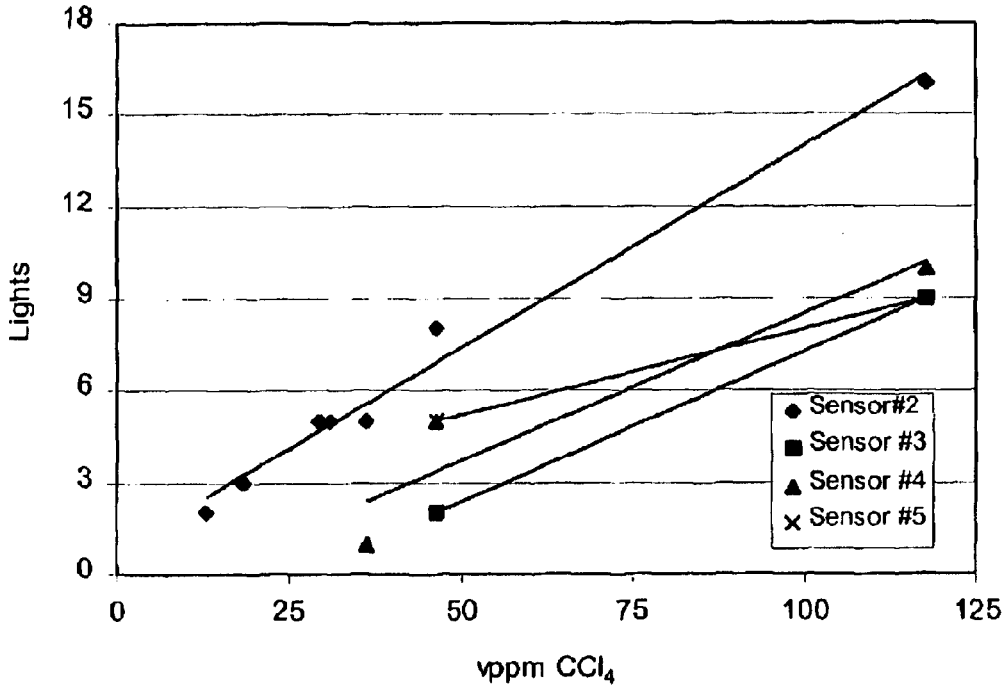
FIG. 20 is a TIF XP-1 Sensitivity Level 4, Sensor Interchangeability
Figure 21:
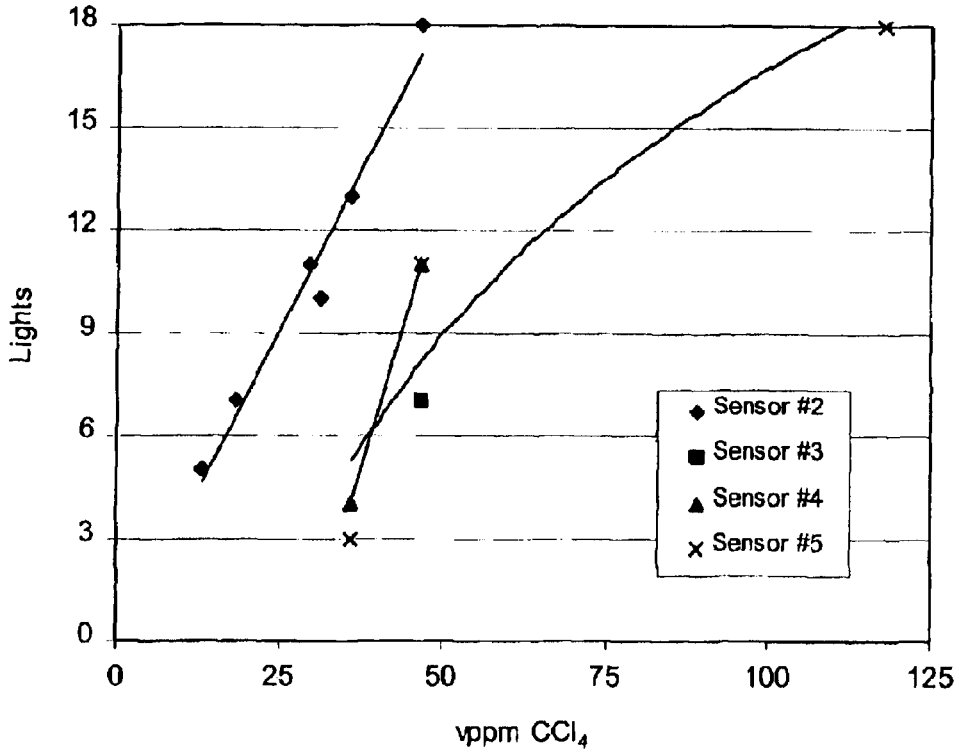
FIG. 21 is a TIF XP-1 Sensitivity Level 5, Sensor Interchangeability
Figure 22:
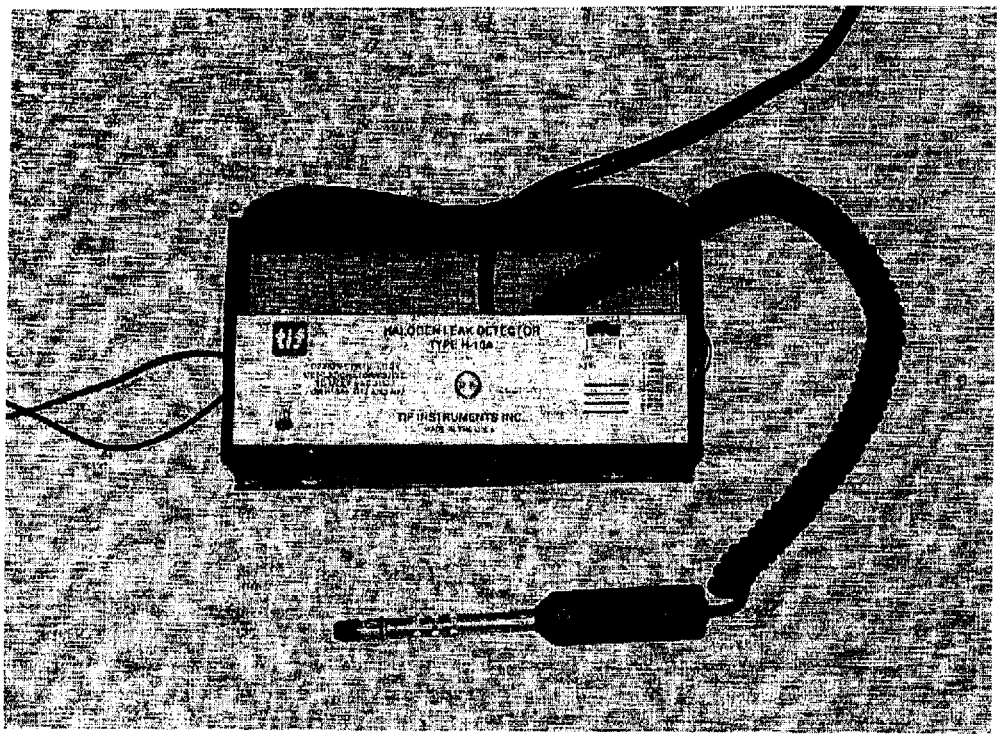
FIG. 22 is a TIF H-10A Leak Detector
Figure 23:
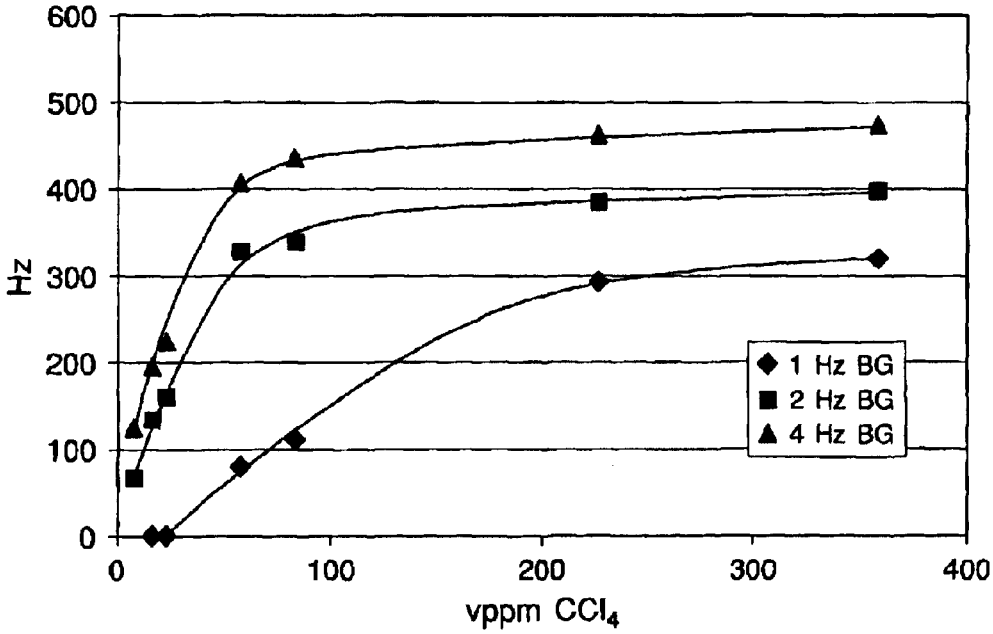
FIG. 23 is a Response Profile of TIF H-10A
Figure 24:
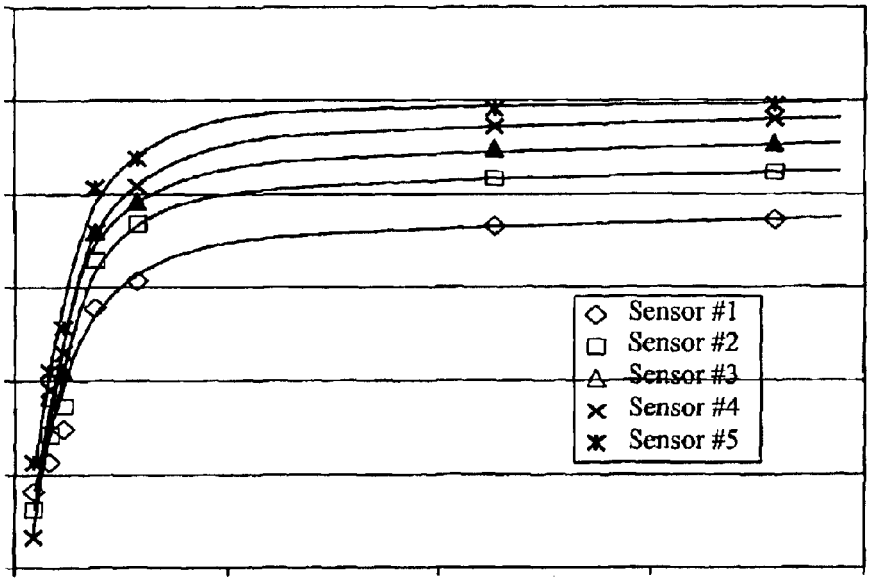
FIG. 24 is TIF H-10A Sensor Interchangeability
Figure 27:
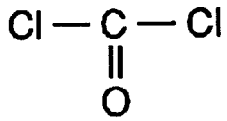
FIG. 27 is Vesicants, Blister Agents
Figure 27:
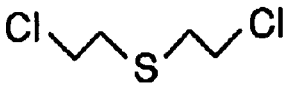
Figure 27:
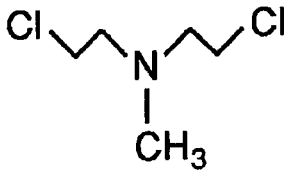

Preferred embodiments of the invention are described herein by presenting the setup of sensor-based examples and the conclusions drawn therefrom.

EXAMPLE DETAILS

Chemicals

Carbon tetrachloride and tetrachloroethylene (perchloroethylene, PCE) were 99.9% ACS reagent grade from Aldrich. Heptane and toluene were reagent grade from VWR. Certified standard solutions of carbon tetrachloride and tetrachloroethylene in methanol at 200 ug/mL were from Supelco.

Heated Diode Leak Detector

The heated diode sensor was a model H-10PM refrigerant leak detector from Yokogowa Corp, Newnan, Ga. An internal sampling pump draws air through a heated diode sensor which operates between temperatures ranging from about 600-1000° C. The sensor selectively interacts with halogens present in the volatile organic compounds that it encounters. This is based on positive ion emission technology, wherein halogens cause an ionized current to flow. The device has an on-board sampling pump which operates at two different flow rates, which control the device's sensitivity. The low flow rate provides the most sensitivity, while the highest flow rate provides the least sensitivity. Sensitivity can also be controlled by adjusting the temperature of the diode heater, with a higher temperature providing greater sensitivity. There is an audio alarm which produces a chirping sound when volatile halogenated compounds are present. Since there is no visual readout, the sensor device was modified by attaching a voltmeter to the electrical output of the sensor so that the voltmeter is responsive to the electrical output. This was accomplished by connecting wires to the output of the signal processing amplifier in the device by CF Electronics, Laramie, WY to provide an output signal which ranges from 0-15 V. The output was connected to a Linseis L200E strip chart recorder. The voltmeter and any other devices necessary to generate a numerical output from the sensor may be referred to as a numerical output provision element. It provides a numerical output (or reading) that is indicative of a concentration of a chemical such as a halogenated volatile compound. Upon such provision the operator of the apparatus obtains or receives a numerical output or reading, perhaps in real time or more generally in short time. The new device may be referred to a halogenated volatile compound sensor apparatus. This halogenated volatile compound may be a halogenated volatile organic compound, as the term halogenated volatile compound in the specification may include halogenated volatile organic compound. Inventive methods related to this sensor (and the corona discharge sensor discussed below) may be referred to as hologenated volatile compound sensing methods Corona Discharge Leak Detector The corona discharge device was a TIF model XP-1 refrigerant leak detector from ATP, Inc., Mirimar, Fla. The mechanical sampling pump to deliver sampled air to the sensor tip did not work well, and thus, detection of chemical vapor is by diffusion only. Note that, as used herein, establishing a sensor in a certain area does not require that the entire sensor be put in that area, but merely that the sensor tip (or other sensitive part of the sensor) be established (or placed or positioned or located, e.g.) in that area. The sensor tip was repeatedly waved or swept over objects, areas, substances or gases to be tested, in an attempt to physically contact the sensor tip with chemical vapors. In order to effectively estimate the location of a chemical leak, the sensor tip was relocated every few seconds to an area void of any chemical vapors, to "re-zero" the sensor. The sensor operates at a potential difference of 1,500 to 2,000 VDC. A discharge current of about 10 microamperes is decreased by the presence of halogen containing VOCs. This perturbation of current is difficult to interpret directly, and the manufacturer has developed a digital signal processing algorithm to convert the change in current or voltage into an audible alarm and a visual readout consisting of a series of light emitting diodes (LEDs) on the front panel which relate to the concentration of contaminant. To provide a stable readout, the device was fitted with a "T" fitting at the sensor tip and a personal sampling pump usually employed for chemical vapor air monitoring in personal hygiene applications to provide an even sample flow across the sensor tip. The pump was configured to pull sampled air past the sensor tip upstream from the pump. The sensor tip was fitted into a low void-volume stainless steel "T" fitting carefully machined to eliminate leakage and to provide consistent air flow past the sensor tip. A TIF model H-10A detector with an air fan in the sensor wand was used also.

The TIF units produce both an audible beep and a light readout when it detects chemical vapors. For the XP-1, the color and number of LED lights is proportional to the amount of chemical vapor detected. For the H-10, the frequency of an audible beep is proportional to the amount of chemical vapor detected. As originally configured, the beeping sound cannot be used to estimate nor quantitate amounts or concentrations of chemical vapors. However, the LED readout can be employed in somewhat simple fashion to gauge the approximate concentration of chemical vapors. One approach may be visually indicative in nature and may involve, for example, a LED readout of three colors and six lights produces a net range of 0 through 18 lights for each of seven sensitivity levels. The most two sensitive levels (levels 6 and 7) exhibited significant background noise, and thus they were not used in the current work. Other visual indicators that indicate the presence and, possibly, the level of concentration of the volatile vapor may be employed. Also, an audible indicator(s) may be used in addition to, or instead of, a visual indicator(s).

A halogenated volatile compound sensor apparatus may be created by modifying a corona discharge sensor by electrically attaching a frequency meter to the H-10A.

The frequency meter and any other devices necessary to generate a numerical output from the sensor may be referred to as a numerical output provision element. It provides a numerical output that is indicative of a concentration of a chemical such as a halogenated volatile compound.

Gas Chromatography

The gas chromatograph (GC) used for the determination of VOCs was a Hewlett-Packard (Agilent Technologies) 5890A equipped with an electron capture detector. The column was a J&W DB-624, 30 m×0.53 mm×30 urn film thickness, operated isothermally at 50° C. (167° F.). The GC results were not affected by the presence or absence of water vapor in the samples.

Tedlar Bag Experiments

Six calibration standards in methanol were prepared from the certified standard solutions in methanol. Volumes of 1 uL of the six calibration standards were injected into the GC, and a linear calibration range was determined.

Saturated headspace vapors of carbon tetrachloride were obtained by pipetting 20 mL of carbon tetrachloride into a 175 mL glass gas-sampling apparatus containing a silicone septum. After overnight liquid/vapor equilibration, the ambient laboratory air temperature was recorded, and uL quantities of saturated headspace vapor were withdrawn through the septum using a gas-tight syringe. These were injected into septum-ported 1 liter and 5 liter Tedlar bags containing dry breathing-quality air introduced from a gas cylinder. Vapor equilibration by diffusion was found to take only a few minutes, and uL quantities of air containing carbon tetrachloride vapor were withdrawn by gas-tight syringe and injected into the GC for analysis to determine ug carbon tetrachloride/L air, and ppmv concentrations.

The probe tip of the Yokogawa heated diode unit was inserted into the Tedlar bag port, after quickly removing the septum. The heated diode sensor responses in volts were recorded using the strip chart recorder wired to the amplified signal outputs. Signal responses from 0 through 15 volts were recorded for the small, medium, and large settings, using the unit's auto mode. Between individual Tedlar bag readings, the unit was re-zeroed using a Tedlar bag blank containing dry air only.

The probe tip of the TIF corona discharge unit was inserted into the bottom port of a carefully machined 316 stainless steel "T" fitting. A 2" piece of PTFE tubing was used to connect one of the top ports to a personal sampling pump, and a second 2" piece of PTFE tubing was used to connect the top port to the Tedlar bag. The corona discharge responses were recorded by counting the number of LED lights illuminated at sensitivity levels 3, 4, and 5. Between individual Tedlar bag readings, the unit was re-zeroed in a Tedlar bag blank with dry air only.

Similar to the dry air environment experiments described above, carbon tetrachloride vapor concentration data were obtained in saturated water vapor environments, using mL quantities of water pipetted into the Tedlar bags. After overnight water liquid/water vapor equilibration at ambient laboratory temperatures, the carbon tetrachloride concentrations were determined by GC, and the responses were determined for the Yokogawa and TIF units. Between individual Tedlar bag readings, the units were re-zeroed using a Tedlar bag blank containing dry air only. Readings from a Tedlar bag containing saturated water vapor alone were obtained also.

The units were also evaluated for their responses to carbon tetrachloride vapor with toluene and n-heptane vapors. Saturated headspace vapors of toluene and n-heptane were prepared in glass gas-sampling apparatuses as described above. Headspace vapors of equal volume amounts to saturated carbon tetrachloride vapors, 10-fold volume amounts, and 100-fold volume amounts were prepared for toluene and n-heptane. Between individual Tedlar bag readings, the units were re-zeroed using a Tedlar bag blank containing dry air only. Readings from Tedlar bags containing various amounts of toluene or n-heptane vapors alone were obtained also.

Results and Discussion

Sensor Response

Sensor response was evaluated by isolating variables such as VOC type, and potential interferences. Responses were evaluated for two distinctly different types of halogenated VOCs, one without double bonds (carbon tetrachloride), and one with a double bond (tetrachloroethylene). The response characteristics were determined for the VOCs directly in headspace, without soil, in Tedlar bags. Quantitation limits were estimated based on a signal to noise ratio of 10 for the Yokogowa heated diode sensor, and at the appearance of three lighted LEDs for the TIF discharge sensor. Potential interferences from volatile hydrocarbons, such as toluene and heptane were evaluated. The effect of humidity was studied also.

a. Heated Diode Sensor

The Yokogawa unit has three sensitivity settings (small, medium, large) which alter the amplified signal by changing both the pump flow rate to the detector and the temperature of the diode, and by attenuation of the electronic signal. Experiments conducted using carbon tetrachloride vapors in sealed air sampling bags containing dry air have shown that the quantitation limit of the unit is approximately 0.2 vapor parts per million (ppmv). Using the most sensitive "small" setting, the lower value of 0.2 ppmv was obtained by strip chart recorder using a signal to noise ratio of 10. Using the least sensitive "large" setting, an upper value of 35 ppmv is in a region where the detector response has become nonlinear. The precise value of the upper working range had not been determined at that time because 35 ppmv is at the upper calibration range of the gas chromatograph used to quantitate the exact concentration of carbon tetrachloride in the bags. Additional experiments can be performed to establish the full dynamic response range, of course.

It has been demonstrated in the laboratory that the presence of saturated water vapor in air samples is not chemically detected in any significant fashion. Moreover, saturated water vapor does not significantly alter the response profile of the detector to carbon tetrachloride. Similarly, the presence of toluene and n-heptane are not chemically detected in significant fashion, and do not significantly alter the response curve profile of the detector to carbon tetrachloride which was determined from 0.2-35 ppmv. Toluene and n-heptane vapors were tested for each point on the response curve at three levels of saturated vapor headspace injected into the Tedlar bags relative to carbon tetrachloride: in equal volumes to carbon tetrachloride, at 10-fold vapor volumes to carbon tetrachloride, and at 100-fold vapor volumes to carbon tetrachloride.

b. Corona Discharge Sensor

The TIF unit has seven sensitivity settings which electronically attenuate the LED lights. In this example, sensitivity level 7 and to a lesser degree, 6, could not be used reliably because they appear to give irreproducible results that bounced and jumped excessively. Experiments conducted using carbon tetrachloride vapors in sealed Tedlar air sampling bags containing dry air have shown that the quantitation limit of the unit is approximately 10 ppmv. Using the sensitivity level 5 setting, the lower value of 10 ppmv was obtained using the least number of lights that yield a reliable quantitation, which is three lights. Levels 3, 4, and 5 were used to explore the working range of the unit. The upper working range of the TIF unit had not yet been determined because 35 ppmv is at the upper calibration range of the gas chromatograph used to quantitate the exact concentration of carbon tetrachloride in the bags. Additional experiments can be performed to establish the full dynamic response range, of course.

The TIF unit gives a chemical response to saturated water vapor in air, which is equivalent to about 20 ppmv of carbon tetrachloride. The response curve of carbon tetrachloride vapor in combination with saturated water vapor is thus the combined sum of the two individual responses. However, it was demonstrated in the laboratory that if the TIF unit is re-zeroed in a saturated water vapor environment, the response curve of carbon tetrachloride vapor in combination with saturated water vapor is roughly equivalent to that of carbon tetrachloride in dry air.

The presence of toluene and n-heptane are not chemically detected in significant fashion, and do not significantly alter the response curve profile of the detector to carbon tetrachloride which was determined from 10-35 ppmv. Toluene and n-heptane vapors were tested for each point on the response curve at three levels of saturated vapor headspace injected into the Tedlar bags relative to carbon tetrachloride: in equal volumes to carbon tetrachloride, at 10-fold vapor volumes to carbon tetrachloride, and at 100-fold vapor volumes to carbon tetrachloride.

Experiment Conclusions

Commercially available heated diode and corona discharge leak detectors were obtained from the manufacturers. These were modified to provide readouts which correspond to the concentration of halogenated VOCs in air. Sensor response was evaluated with carbon tetrachloride. The response characteristics were determined for the VOCs directly in headspace, without soil, in containers such as in Tedlar bags. Quantitation limits were estimated. Potential interferences from volatile hydrocarbons, such as toluene and heptane were evaluated. The effect of humidity was studied also.

TABLE 5

PID Detectability for Volatile Organic Compounds

| Compound | PID Detectability 10.6 eV | PID Detectability 11.7 eV |
|---|---|---|
| Dichloromethane (Methylene chloride) | N | Y |
| Trichloroethylene | Y | Y |
| Tetrachloroethylene | Y | Y |
| trans-1,2-Dichloroethylene | Y | Y |
| Trichloromethane (Chloroform) | N | Y |
| 1,1-Dichloroethane | N | Y |
| 1,1-Dichloroethylene | Y | Y |
| 1,1,1-Trichloroethane | N | Y |
| Toluene | Y | Y |
| 1,2-Dichloroethane | N | Y |
| Benzene | Y | Y |
| O-Xylene | Y | Y |
| Ethylbenzene | Y | Y |
| Vinyl chloride | Y | Y |
| Carbon tetrachloride | N | Y |
| Chlorobenzene | Y | Y |
| p-Dichlorobenzene | Y | Y |
| Naphthalene | Y | Y |

Figure 28:
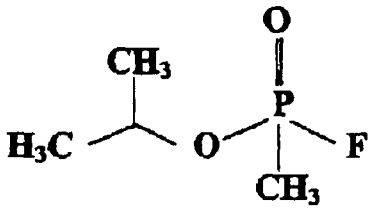
FIG. 28 is a representation of examples of Halogen containing volatile organic compounds.
Figure 28:
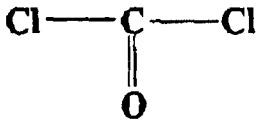
Figure 28:
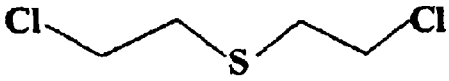

The present invention involves a screening methodology and a portable test kit to measure and distinguish substances such as halogenated volatile organic compounds (VOCs) in the field. One embodiment involves the use of heated diode and corona discharge sensors such as are commonly used as alarm sensors to detect leaks of refrigerants from air conditioners, freezers, and refrigerators. These are capable of detecting the presence of halogens or carbon-halogen bonds. Further, commercially available and inexpensive heated diode and corona discharge leak detectors can be adapted to provide a numerical signal related to VOC concentration as well as to detect specific CMAs. As one example, halogen-containing chemical warfare agents including sarin, phosgene, and mustard gas (as depicted in FIG. 28) may be individually detected and reacted to.

The invention may also involve an air sampling train of multiple sensors constructed using a variety of chemical detection sensor technologies in a chemical vapor sensor array apparatus. It may include existing detectors may modified to maximize their sensitivity, or unmodified existing sensors. Further, multiple sensors may be sequenced for a desired result. It is important to understand that, as used herein, the phrase "at least one other sensor" is characteristic of not only a different type of sensor, but also of a different, discrete sensor (i.e. the at least one other sensor can be the same as the referenced sensor). Non-destructive chemical detectors may be configured up stream from destructive detectors in airflow channels which may even separately condition the air to be sensed. Air may be sampled using precise pumps or mass flow controllers. Construction may be in a wall-mounted box for passive sampling, in a portable field unit, or in other arrangements. Initial and periodic calibration of the detector array or sensor array (or chemical vapor sensor array) may be accommodated, and subsequent detector signals or sense outputs could even be collected by a multivariate analysis element such as a central computing device employing pre-programmed logic schemes to interpret results, thereby said multivariate analysis element may operate on sense outputs to generate (perhaps in real time) a sensible indication as to the concentration of a chemical functional group. The term "sensible indication as to concentration of a chemical functional group" (regardless of what type of chemical functional group it is), is intended to refer to not only an indication as to the actual concentration of the group (which may be merely one type of chemical), but also to an indication of merely whether that group exists (i.e., its presence). The multivariate analysis element could function to provide information as to the presence and/or concentration of a chemical functional group. As one example, a positive signal by both photoionization and heated diode sensors may be interpreted as indicative of a halogenated chemical with a double bond; a positive signal by thermal conductivity could indicate a relatively high level of aliphatic hydrocarbon; signal ratio data, perhaps previously stored in a unit's microprocessor could be applied to interpret the various detector signals, and possibly to identify an individual compound such as a volatile chemical warfare agent, or halogenated volatile chemical warfare agent. As such, one goal of the invention would be to provide a cost-effective means to analyze chemical vapors in air for a variety of purposes, including environmental, security, and defense applications. Importantly, the term environmental monitoring is a term of art (i.e., environment here has a different scope than surroundings), and generally refers to, as but a few examples, groundwater monitoring (for contaminants, e.g.), soil monitoring and air monitoring. Testing for refrigerant leaks near a device using refrigerant is not considered environmental monitoring. The term environmental area of interest is also accorded such a meaning.

In an embodiment of the invention using an air sampling train of single or multiple sensors, there may be a configuration of cells or tubes or fibers containing materials that may selectively prevent certain selected classes of chemicals from passing through. These may permit separate conditioning for individual sensors. This could allow for additional degrees of selectivity in such devices. In one embodiment, the system may differentiate between classes of chemicals by using selective adsorption (via a selective adsorption element), absorption (via a selective absorption element), or reaction (via a selective reaction element) of a particular class of chemicals by passing them through a cell, tube, filter, or fiber or other selective chemical group removal element comprising materials which may prevent their passage. There may be a sensor at the inlet and another sensor at the outlet of the tube and the two may be combined to permit an appropriate determination. Chemicals that do not adsorb or absorb or react with the cell contents may pass through and be detected by both sensors. Chemicals that do not pass through may be detected by only the one sensor at the inlet of the tube. Such are merely a few ways in which a chemical functional group (which may include one chemical type) can be sensed (either to assess its presence and/or to determine its concentration). Such a chemical functional group may be further characterized as a volatile compound functional group, or a halogenated functional group, or a halogenated chemical warfare agent group, as but a few examples.

For example, sarin reacts readily with water. One configuration of a sensor device could be a halogen-selective sensor placed at the inlet of a cell containing water, either bound or as a liquid. A second identical sensor could be placed at the cell outlet. The air containing sarin would be passed across the first sensor, through the cell (or sarin removal element, in this case), and across the second sensor. Sarin would be detected by the first sensor, but not the second. Halogen-containing refrigerants such as the Freons or their replacements, or solvent vapors such as methylene chloride or tetrachloroethylene might pass through the wet cell and thus they would be detected by both sensors permitting a differentiation. Either levels of response, types of response, or any other factor may be utilized to permit an appropriate determination or differentiation. Environmentally sensitive substances that may detected or distinguished may include: Dichloromethane (Methylene chloride), Trichloroethylene, Tetrachloroethylene, trans-1,2-Dichloroethene, Trichloromethane (Chloroform), 1,1-Dichloroethane, 1,1-Dichloroethene, 1,1,1-Trichloroethane, Toluene, 1,2-Dichloroethane, Benzene, o-Xylene, Ethylbenzene, Vinyl chloride, Carbon tetrachloride, Chlorobenzene, p-Dichlorobenzene, Naphthalene, and others.

Sensor response relative to carbon tetrachloride and tetrachloroethylene (perchloroethylene, PCE) which represent halogenated VOCs with and without double bonds may also be used. The detectors may be configured to give a different response for PCE relative to carbon tetrachloride. Qualitative information leading to possible compound or compound type identification can also be obtained by using multiple sensors together and taking a ratio of their signals. Environmental analysis applications may also be available. Configuration may also be selected so that potential interferences from volatile hydrocarbons, such as toluene and heptane may not significantly affect the response from one or more detectors. The effect of humidity may also be included and detectors may be selected to either not respond significantly to humidity or perhaps even for any response to humidity to be zeroed out as background either upon setup, upon start up, or by automatic operation.

Sensors may also be chosen to detect halogen-containing volatile chemical warfare agents in air at low levels. Halogen-containing chemical warfare agents (CWA) including at least sarin, phosgene, and mustard gas may be specified by the design or software. An ability to differentiate between halogenated CWAs and halogenated VOCs such as halogenated dry cleaning or degreasing solvents or refrigerants may be included. This could avoid false alarms, and in a civilian setting, panic and mass hysteria.

For cost savings, modified refrigerant leak detectors may be used. With the addition of more detector technologies, the device may even be adaptable to detect a variety of non-halogenated VOCs and CWAs and to even identify individual compounds or compound classes, or to rule out specific interferences that might give a signal with one of the sensors either on initial design, or as more frequent occurrences arise. A detector array containing both heated diode and corona discharge halogenated-selective sensors configured with other sensor types such as thermal conductivity, photoionization, hydrocarbon detectors, and others can be used. In addition, the use of selective removal of analytes between sensors using adsorption, absorption, or reaction can be applied to gain additional degrees of selectivity. These can be combined with any sensor combination.

The system may provide a cost-effective means to rapidly screen for halogenated VOCs or chemical warfare agents in the field. Existing refrigerant detector alarm monitors with slight hardware modification and analytical method adaptation may be used for specific utility. Of course a variety of configurations are possible as well as a variety of detectors. Another goal of the invention is to provide a cost-effective means to differentiate between species, such as halogenated chemical warfare agents, possible in air and other halogenated compounds such as refrigerants, dry cleaning solvents, and degreasing solvents. Yet another goal is to provide for the selective detection of chemical vapors such as in air or otherwise.

In an array system, computer software for multi-variate analysis may be used. This could be based on commercially available or custom-written software. Potential system capabilities or features for different embodiments include, but are not limited to:

- providing a wall-mounted, passive device, perhaps like a smoke detector in appearance;
- providing potentially an integrated, hand-held device (such as a handheld chemical vapor sensor array apparatus);
- utilizing an array of sensors;
- utilizing an array of commercially available sensors modified to detect and identify volatile CWAs perhaps released in air;
- providing analysis results within seconds, or more generally a short time (which, as used herein, refers to any one of less than 1 second, less than 3 seconds, less than 5 seconds, less than 10 seconds, less than 30 seconds, or less than that of any existing apparatus) (real time as used herein refers to less than one second);
- providing a systems with a varied CWA target list including but not limited to GA, GB, GD, AC, CK, CG, chlorine, nitrogen and sulfur mustard, and in non-volatile sensor systems, perhaps VX;
- providing and deploying a system designed or positioned for use in public areas such as subways, airport terminals, sports arenas, malls, etc.;
- providing a system which may be battery powered, perhaps as a backup to regular AC power for high reliability; and
- providing a system capable of being interfaced with facility CWA defense systems perhaps to automatically trigger an official reaction/notification a release of an appropriate counter agent or chemical treatment (perhaps as simple as a release of water such as in a spray fire extinguisher system [water destroys some agents such as GB and GD]) or, more generally, a response which is designed to mitigate or to render the CWA harmless, and/or to automatically elicit any other appropriate security response.
- obtaining at least two volatile compound sensors; arranging sensors in an array so that each may sense a gas of interest (such as air in a headspace above water or soil, e.g.); initiating operation of the sensors (as by activating a switch); and obtaining a sensible indication relative to a concentration of a volatile compound functional group As should be understood, the system may be configured using any combination or a great variety of sensor techniques. Detectors include a large variety of possibilities. One instrument adaptable for field (or in-field) screening for VOCs is a hand-held photoionization detection (PID) instrument. While PID detectors suffer from a disadvantage in that they cannot discriminate between halogenated and non-halogenated species the above designs may be applied to overcome deficiencies. Another type of portable detector is the portable gas chromatograph. Again, although when used alone, this type of detector requires skilled operators, it may be adapted for easy use. Existing refrigerant detectors and alarm monitors may be used perhaps with only slight hardware modification. Heated diode and corona discharge monitor technology may be utilized. Heated diode leak monitors such as are available from Bacharach, Inc. in Newnan, Ga. may be applied operating on 12 volts at less than 1 amp. A refrigerant leak detector such as a TIF model XP-1 from ATP, Inc. may be used. This is a corona discharge device with a discharge current of about 10 microamperes which is decreased by the presence of halogen-containing VOCs. A TIF H-10A can be utilized and operated on 115 V. Other corona discharge leak monitors such as are available from TIF Instruments, Inc., Mirimar, Fla. may be applied. Detectors may include high-impedance circuits operating at about 1,500 to 2,000 volts at the detector tip. Immunoassay kits can be used and existing designs may be perhaps adapted for rapid field analysis. Even though the immunoassay approach can require temperature control and critical timing and a sequence of steps such may be automated. Surface and down-hole screening of halogenated VOCs in the field can be used. Refractive index attenuation on coated optical fibers can be used. Chemical reaction in a basic media to form a color in the presence of trichloroethylene is possible. A radio frequency-induced helium plasma optical emission spectrometer can be used. Probes using a $LaF_2$-doped element heated to about 600° C. (1,112° F.) can be used. A synthetic nose consisting of an array of different chemicals that give different optical responses to various volatile analytes may be applied. Raman spectroscopy, detectors for volatile DNAPLs, detectors to measure aromatic rings by ultraviolet light absorption, detectors which ionize compounds containing double bonds, detectors using a lithium fluoride window, electrochemical cells, acoustic wave devices, and ion mobility spectrometry are each possible. These and others types of detectors are detailed in several of the articles and other documents incorporated by reference in this application. For example, one heated diode sensor could be a device such as applied in model H-10PM refrigerant leak detector from Yokogowa Corp, Newnan, Ga. Devices as shown in U.S. Pat. Nos. 3,979,625 and 3,991,360 and 4,151,641 (each hereby incorporated by reference) may be employed. A corona discharge device such as TIF model H-10A refrigerant leak detector from Advanced Test Products, Inc., Mirimar, Fla. or as shown in U.S. Pat. Nos. RE32,552 and 3,742,475 (each hereby incorporated by reference) could be included. Other devices which could be used in particular embodiments include but are not limited to: a photoionization detector, a combustible hydrocarbon sensor, a thermal conductivity detector, an electrochemical cell, a quartz crystal microbalance, a surface acoustic wave device, an optical spectrometer (ultraviolet, visible, infrared, fluorescence, phosphorescence, raman, or photoacoustic), an ultrasonic sensor, a heat capacity transducer, other gas-selective sensors. Key here is that with the teachings of this invention and a knowledge of the agents of interest, specific reactions may be achieved and assured.

The detector system also may be designed to work in an environment of varying and often high relative humidity. Response characteristics and background levels may be evaluated at different relative humidities and may be accommodated by the system. Potential interferences from aliphatic or aromatic hydrocarbons may be designed to be minimal. The system may also be designed to demonstrate a significant selectivity to halogenated VOCs in the presence of non-halogenated VOCs.

A digital readout or other indication may be included. Sensible indication (which may be real time in at least one embodiment) as used herein refers to an indication that can be sensed by a human or perhaps an apparatus. In other embodiments, an audible alarm and a visual readout consisting of a series of lighted diodes on the front panel that relate to the concentration of contaminant may be included. An audible beep and an LED readout can be used with or without the frequency of the beep, and the color and/or number of LED lights being designed to be proportional to the amount of chemical vapor detected. An LED readout of three colors and six lights can be configured to produce a net signal range of 0 through 18 lights for each of a variety of sensitivity levels. Such levels may also electronically attenuate the signal from the detector. A flashing neon light and an audible popping signal (perhaps personalized to prevent hysteria) that increases in frequency as higher amounts of agent are sensed can be included. Frequencies from about 1-300 Hz can be used and any aspect can even be recorded for historical, comparison, or verification purposes. Outputs which enable the user to "home-in" on the location of a chemical source (perhaps using a chemical functional group source location element responsive to the sensors) can be included. A steady-signal readout can be used and can be configured to provide quantitative or semiquantitative determination of halogenated VOCs or other substances in the field.

Figure 29:
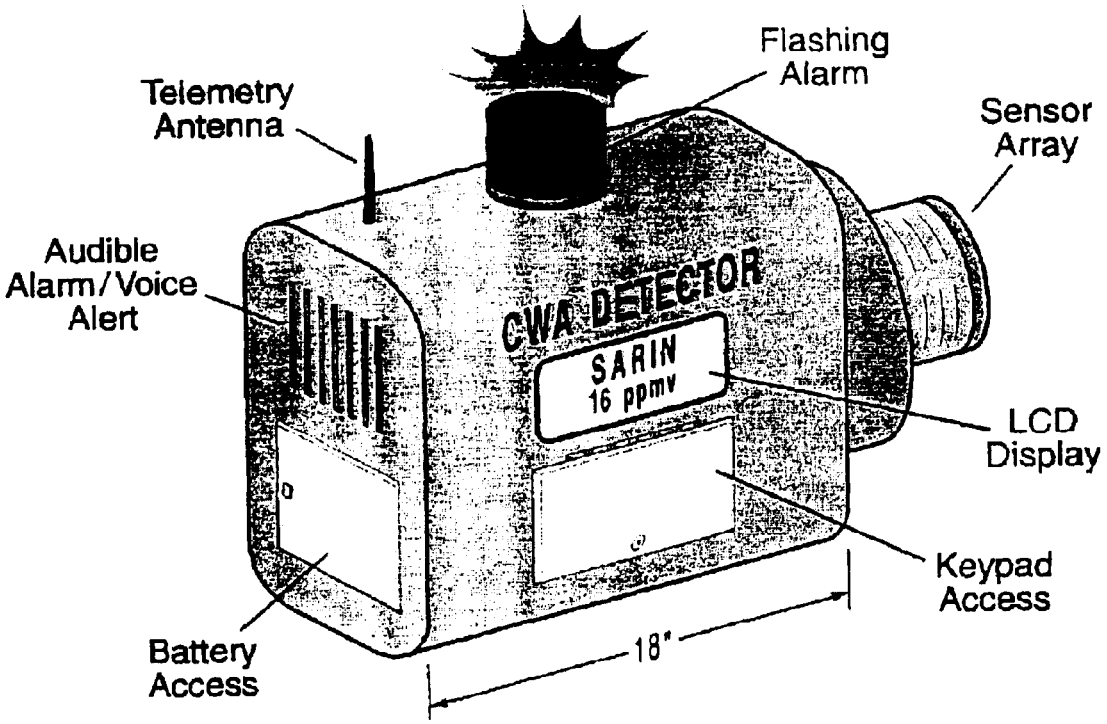
FIG. 29 is a device which could be deployed as a wall-mounted unit such as a smoke detector

As shown in FIG. 29, for CWA detection, a device could be deployed as a wall-mounted unit such as a smoke detector. Positive identification could cause an alarm to sound or send a signal to a security office. Possibly hand portable versions of these devices could be developed also. Applications could include CWA detection and other applications for VOC detection including environmental screening and emergency response. The system may be designed as an integrated, self contained device. It may include a small fan within the body of the unit to pull sampled air past the appropriate detector(s) at a constant flow perhaps using a low-void volume stainless steel fitting perhaps carefully machined to eliminate leakage and void volumes, and to provide consistent air flow. Air flows of about 150 mL/min may be used.

As can be easily understood from the foregoing, the basic concepts of the present invention may be embodied in a variety of ways. It involves both detection techniques as well as devices to accomplish the appropriate detection. In this application, the detection techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for the full patent application. It should be understood that such language changes and broad claiming will be accomplished when the applicant later (filed by the required deadline) seeks a patent filing based on this provisional filing. This full patent application may seek examination of as broad a base of claims as deemed within the applicant's right and will be designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sensor" should be understood to encompass disclosure of the act of "sensing"—whether explicitly discussed or not—and, conversely, were there effectively disclosure of the act of "sensing", such a disclosure should be understood to encompass disclosure of a "sensor" and even a "means for sensing." Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement or reference statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the detection devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, xi) processes performed with the aid of or on a computer or computational device as described throughout the above discussion, xii) a programmable apparatus as described throughout the above discussion, xiii) a computer readable memory encoded with data to direct a computer comprising means or elements which function as described throughout the above discussion, xiv) a computer configured as herein disclosed and described, xv) individual or combined subroutines and programs as herein disclosed and described, xvi) the related methods disclosed and described, xvii) similar, equivalent, and even implicit variations of each of these systems and methods, xviii) those alternative designs which accomplish each of the functions shown as are disclosed and described, xix) those alternative designs and methods which accomplish each of the functions shown as are implicit to accomplish that which is disclosed and described, xx) each feature, component, and step shown as separate and independent inventions, xxi) the various combinations and permutations of each of the above, xxii) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any acts of law, statutes, regulations, or rules mentioned in this application for patent; or patents, publications, or other references mentioned in this application for patent, are each hereby incorporated by reference. Specifically, U.S. patent application Ser. No. 60/340,561, filed Dec. 13, 2001 and U.S. patent application Ser. No. 60/405,638; filed Aug. 23, 2002 are hereby incorporated by reference including any figures or attachments. Any Exhibits mentioned or included within this application, specifically Exhibits 1 and 2, are hereby incorporated by reference, as are any tables.

In drafting any claims at any time whether in this provisional application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Exhibit 1

WRI-02-R013

FIELD SCREENING FOR HALOGENATED VOLATILE ORGANIC COMPOUNDS

Topical Report

By
John F. Schabron
Joseph F. Rovani, Jr.
Theresa M. Bomstad

June 2002

Work Performed Under Cooperative Agreement
DE-FC26-98FT40322 Task 3.8

For
U.S. Department of Energy
Office of Fossil Energy
National Energy Technology Laboratory
Morgantown, West Virginia By
Western Research Institute
Laramie, Wyoming

What is claimed is:

1. A method of sensing an environmentally situated, non-refrigerant halogenated volatile compound comprising the steps of:

[obtaining a refrigerant leak detector from which an] *utilizing corona discharge and/or heated diode sensor technology to contact a sample suspected of containing said environmentally situated, non-refrigerant halogenated volatile compound and obtain an* electrical output [can be obtained]; and

[establishing] *utilizing* a numerical output provision element responsive to said electrical output [for] *to* quantitatively [displaying] *display* a value of a concentration of said environmentally situated, non-refrigerant halogenated volatile compound, wherein said *sample suspected of containing said* environmentally situated, non-refrigerant halogenated volatile compound is in an environmental area of interest.

2. A method of sensing an environmentally situated, non-refrigerant halogenated volatile compound as described in claim 1, wherein said [step of establishing a numerical output provision element responsive to said electrical output for quantitatively displaying a value of a concentration of an] environmentally situated, non-refrigerant halogenated volatile compound comprises [the step of establishing a numerical output provision element responsive to said electrical output and that quantitatively displays a value of a concentration of] a halogenated soil contaminant.

3. A method of sensing an environmentally situated, non-refrigerant halogenated volatile compound as describe in claim 1, wherein said [step of establishing a numerical output provision element responsive to said electrical output for quantitatively displaying a value of a concentration of an] environmentally situated, non-refrigerant halogenated volatile compound comprises [the step of establishing a numerical output provision element that quantitatively displays a value of a concentration of] an environmentally situated, non-refrigerant halogenated volatile compound in the presence of non-halogenated volatile compounds.

4. A method of sensing environmentally situated, non-refrigerant halogenated volatile compound as described in claim 1, wherein said [step of establishing a numerical output provision element responsive to said electrical output and that quantitatively displays a value of a concentration of an] environmentally situated, non-refrigerant halogenated volatile compound comprises [the step of establishing a numeric output provision element responsive to said electrical output and that quantitatively displays a value of a concentration of] a DNAPL that [contaminate] *contaminates* oil or water.

5. A method of sensing an environmentally situated, non-refrigerant halogenated volatile compound and described in claim 1, wherein said [step of establishing a numerical output provision element responsive to said electrical output and that quantitatively displays a value of a concentration of an] environmentally situated, non-refrigerant halogenated volatile compound comprises [the step of establishing a numeric output provision element responsive to said electrical output and that quantitatively displays a value of a concentration of] a halogenated volatile compound chemical warfare agent.

[6. A method of sensing an environmently situated, non-refrigerant halogenated volatile compound as described claim 1, wherein said step of establishing a numerical output provision element responsive to said electrical output for quantitatively displaying a value a concentration of an environmentally situated, non-refrigerant halogenated volatile compound comprises the step of establishing a numeric output provision element responsive to said electrical output and that quantitatively displays a value of a concentration of said environmentally situated, non-refrigerant halogenated volatile compound.]

7. A method of environmental monitoring for environmentally situated, halogenated volatile compounds comprising the steps of:

[obtaining a refrigerant leak detector adapted to provide a value of a concentration of an environmentally situated, halogenated volatile compound;]

[establishing said refrigerant leak detector] *positioning corona discharge and/or heated diode sensor technology* in an environmental area of interest *to contact a sample suspected of containing said environmentally situated, non-refrigerant halogenated volatile compound*; [and]

sensing said environmentally situated, halogenated volatile compound in said environmental area of interest by operating said [refrigerant leak detector] *corona discharge and/or heated diode sensor technology to provide a value of a concentration of said environmentally situated, halogenated volatile compound*; and quantitatively displaying said value of [a] *said* concentration of said environmentally situated, halogenated volatile compound.

8. A method of environmental monitoring for environmentally situated, halogenated volatile compounds as described in claim 7, wherein said [step of sensing an] environmentally situated, halogenated volatile compound comprises [the step of sensing] halogenated contaminants.

9. A method of environmental monitoring for environmentally situated, halogenated volatile compounds as described in claim 7, wherein said [step of obtaining a refrigerant leak detector] *corona discharge and/or heated diode sensor technology* comprises [the step of obtaining] a commercially available refrigerant leak detector.

10. A method of environmental monitoring for environmentally situated, halogenated volatile compounds as described in claim 7 or 9 wherein said [step of obtaining a refrigerant leak detector] *corona discharge and/or heated diode sensor technology* comprises [the step of obtaining] a heated diode refrigerant leak detector.

11. A method of environmental monitoring for environmentally situated, halogenated volatile compounds as described in claim 7 or 9 wherein said [step of obtaining a refrigerant leak detector] *corona discharge and/or heated diode sensor technology* comprises [the step of obtaining] a corona discharge refrigerant leak detector.

12. A method of environmental monitoring for environmentally situated, halogenated volatile compounds as described in claim 7, wherein said step of [obtaining a refrigerant leak detector] *operating said corona discharge and/or heated diode sensor technology to provide a value of a concentration of said environmentally situated, halogenated volatile compound* comprises the step of obtaining [a refrigerant leak detector from which] an electrical output [can be obtained] *from said corona discharge and/or heated diode sensor technology* and further comprising the step of [establishing] *utilizing* a numerical output provision element responsive to said electrical output *to provide said value of the concentration of said environmentally situated, halogenated volatile compound*.

13. A method of environmental monitoring for environmentally situated, halogenated volatile compounds as described in claim 12, wherein said [step of establishing a] numerical output provision element responsive to said electrical output comprises [the step of connecting] a voltmeter *connected to said corona discharge and/or heated diode sensor technology* in order to provide said numerical output.

14. A method of environmental monitoring for environmentally situated, halogenated volatile compounds as described in claim 12, wherein said [step of establishing a] numerical output provision element responsive to said electrical output comprises [the step of connecting] a frequency meter *connected to said corona discharge and/or heated diode sensor technology* in order to provide said numerical output.

15. A method of environmental monitoring for environmentally situated, halogenated volatile compounds as described in claim 7, wherein said [step of establishing said refrigerant leak detector in an] environmental area of interest comprises [the step of establishing said refrigerant leak detector in] soil or [in] a headspace above *said* soil.

16. A method of environmental monitoring for environmentally situated, halogenated volatile compounds as described in claim 7, wherein said [step of sensing a] halogenated volatile compound in said environmental area of interest [by operating said refrigerant leak detector] comprises [the step of sensing] a halogenated volatile chemical war agent selected from the group [of a halogenated volatile chemical war agents] consisting of: sarin, soman, cyanogen chloride, chlorine, phosgene, sulfur mustard, nitrogen mustard and lewisite.

17. A method of environmental monitoring for environmentally situated, halogenated volatile compounds as described in claim 7, further comprising the step of [establishing] *utilizing* an alert system responsive to said step of sensing a halogenated volatile compound in said environmental area of interest by operating said [refrigerant leak detector] *corona discharge and/or heated diode sensor technology to provide a value of a concentration of said environmentally situated, halogenated volatile compound*.

18. A method of environmental monitoring for environmentally situated, halogenated volatile compounds as described in claim 7, wherein said step of sensing comprises in-field sensing of a halogenated volatile compound in soil, water or air.

19. A method of environmental monitoring for environmentally situated, halogenated volatile compounds as described in claim 7, wherein said [step of establishing said refrigerant leak detector in an] environmental area of interest comprises [the step of establishing said refrigerant leak detector in] a headspace above soil.

20. A method [environmental] *of environmental* monitoring for environmentally situated, halogenated volatile compounds as described in claim 7, wherein said [step of establishing said refrigerant leak detector in an] environmental area of interest comprises [step of establishing said refrigerant leak detector in] a headspace above water.

21. A method of environmental monitoring for environmentally situated, halogenated volatile compounds as described in claim 7, wherein said [step of establishing said refrigerant leak detector in an] environmental area of interest comprises [the , step of establishing said refrigerant leak detector in] air.

22. A method of environmental monitoring for environmentally situated, halogenated volatile compounds as described in claim 7, wherein said [step of sensing said] environmentally situated, halogenated volatile compound [in said environmental at of interest by operating said refrigerant leak detector] comprises [the step sensing] an environmentally situated, non-refrigerant halogenated volatile compound.

*23. A method of sensing an environmentally situated, non-refrigerant halogenated volatile compound as described in claim 1, wherein said corona discharge and/or heated diode sensor technology comprises a refrigerant leak detector.*

*24. A method of sensing an environmentally situated, non-refrigerant halogenated volatile compound as described in claim 23, wherein said refrigerant leak detector comprises a commercially available refrigerant leak detector.*

*25. A method of sensing an environmentally situated, non-refrigerant halogenated volatile compound as described in claim 4, further comprising the step of utilizing an alert system responsive to said step electrical output of said corona discharge and/or heated diode sensor technology.*

*26. A method of an sensing environmentally situated, non-refrigerant halogenated volatile compound as described in claim 1, wherein said numerical output provision element responsive to said electrical output for quantitatively displaying a value of a concentration of an environmentally situated, non-refrigerant halogenated volatile compound comprises a voltmeter or a frequency meter connected to said corona discharge and/or heated diode sensor technology.*

*27. A method of environmental monitoring for environmentally situated, halogenated volatile compounds as described in claim 7, wherein said corona discharge and/or heated diode sensor technology is commercially available.*

*28. A method of environmental monitoring for environmentally situated, halogenated volatile compounds as described in claim 7, wherein said corona discharge and/or heated diode sensor technology provides a numerical value of said concentration of an environmentally situated halogenated volatile compound.*

*29. A method of environmental monitoring for environmentally situated, halogenated volatile compounds as described in claim 7, wherein said environmentally situated halogenated volatile compound comprises an environmentally situated, halogenated volatile organic compound.*

* * * * *